United States Patent [19]
Takeuchi et al.

[11] Patent Number: 5,886,167
[45] Date of Patent: Mar. 23, 1999

[54] 2'-DEOXY-2'-EPI-2'-FLUOROCOFORMYCIN

[75] Inventors: Tomio Takeuchi; Sumio Umezawa, both of Tokyo; Tsutomu Tsuchiya, Yokohama; Yoshiaki Takahashi, Tokyo, all of Japan

[73] Assignee: Zaidan Hojin Biseibutsu Kagaku Kenkyu Kai, Tokyo, Japan

[21] Appl. No.: 990,461

[22] Filed: Dec. 15, 1997

Related U.S. Application Data

[62] Division of Ser. No. 620,396, Mar. 22, 1996, Pat. No. 5,773,607, which is a continuation of Ser. No. 240,777, filed as PCT/JP92/01489 Nov. 13, 1992, abandoned.

[30] Foreign Application Priority Data

Nov. 1, 1991 [JP] Japan ..................................... 3-352588

[51] Int. Cl.$^6$ ..................................... C07H 19/16
[52] U.S. Cl. .................. 536/27.21; 536/22.1; 536/27.13; 536/28.8; 536/29.1; 549/475; 549/480; 549/504
[58] Field of Search ................................ 536/22.1, 27.13, 536/28.8, 29.1, 27.21; 549/475, 480, 504

[56] References Cited

U.S. PATENT DOCUMENTS 4,625,020 11/1986 Brundidge et al. ..................... 536/18.2
4,713,372 12/1987 Schaumberg et al. ..................... 514/45

FOREIGN PATENT DOCUMENTS 0156524 10/1985 European Pat. Off. .
0509470 10/1992 European Pat. Off. .
2517596 10/1975 Germany .
92/10198 6/1992 WIPO .

OTHER PUBLICATIONS

Jackson et al. Adv. Enzyme Regal. 1986, 25, 125–39.
Tanaka et al. Novel Microb. Prod. Med. Agric. 1989, 67–72.
Schramm et al. Biochemistry 1985, 24(3), 641–6.
Woo et al. J. Labelled Compd. Radiopharm. 1990, 28(4), 445–54.
Showalter et al. J. Med. Chem. 1983, 26, 1478–1482.

*Primary Examiner*—Kathleen K. Fonda
*Attorney, Agent, or Firm*—Larson & Taylor

[57] ABSTRACT

2'-Deoxy-2'-fluorocoformycin and 2'-deoxy-8-epi-2'-fluorocoformycin are synthesized in this invention through a multi-stage process via 3,5-di-O-benzoyl-2-deoxy-2-fluoro-α- and -β-D-ribofuranosyl bromides. Further, according to this invention, 2'-deoxy-2'-epi-2'-fluorocoformycin and 2'-deoxy-8,2'-diepi-2'-fluorocoformycin are synthesized by a multi-stage process starting from 3,5-di-O-benzoyl-2-deoxy-2-fluoro-α-D-arabinofuranosyl bromide. These four 2'-fluoro derivatives of coformycin are novel compounds and have high enzyme-inhibitory activities against adenosine deaminase. In particular, these novel compounds are useful substances which exhibit therapeutic effects on acute lymphocytic leukemias due to their high enzyme-inhibitory activities above-mentioned. In addition, a variety of intermediates are obtained as novel compounds which are useful for the synthesis of the aforesaid novel 2'-fluoro derivatives of coformycin.

1 Claim, No Drawings

2'-DEOXY-2'-EPI-2'-FLUOROCOFORMYCIN

This is a division of application Ser. No. 08/620,396 filed Mar. 22, 1996, now U.S. Pat. No. 5,773,607; which is a continuation of Ser. No. 08/240,777, filed as PCT/JP92/01489 Nov. 13, 1992, now abandoned.

TECHNICAL FIELD

This invention relates to 2'-deoxy-2'-fluorocoformycin and stereoisomers thereof as novel compounds which are of low toxicity, possess strong enzyme-inhibitory activities against adenosine deaminase, exhibit anti-tumor activities useful for therapeutic treatments of lymphocytic leukemias and lymphomas and also exhibit anti-bacterial activities against gram-negative bacteria in the presence of formycin A.

This invention further relates to a 2-deoxy-2-fluoro-α,β-D-ribofuranosyl halide and 2-deoxy-2-fluoro-α,β-D-ribofuranosyl or -arabinofuranosyl azide, all of which are useful as novel intermediates for the synthesis of 2'-deoxy-2'-fluorocoformycin or stereoisomers thereof, and also this invention relates to 2-deoxy-2-fluoro-α,β-D-ribofuranosyl or -arabinofuranosyl amine which is useful as an intermediate and as an antibacterial agent.

This invention further relates to 5-amino-1-(2-deoxy-2-fluoro-β-D-ribofuranosyl or -arabinofuranosyl)-imidazole-4-carboxylic acid and 3-(2-deoxy-2-fluoro-β-D-ribofuranosyl or -arabinofuranosyl)-6,7-dihydroimidazo-[4,5-d][1,3]diazepin-8(3H)-one, all of which are useful novel intermediate compounds.

BACKGROUND ART

Adenosine deaminase is an enzyme which is widely present in vivo in mammals and which parcipitates in the conversion of adenosine to inosine in the course of the synthesis of purine and in salvage pathway. Adenosine deaminase is known to exist predominantly in lymphocytic cells.

Coformycin possesses an activity inhibitory to adenosine deaminase enzymes and is known as an antibiotic of nucleoside-type which is capable of enhancing the activity of formycin A having an antitumor activity [see, for example, the specification of Japanese Patent Publication Sho-45-12278 and "The Journal of Antibiotics" A20, p.227 (1967)]. Further, coformycin exhibits an antibacterial activity in the presence of formycin A. However, coformycin has such drawback that it is un-stable in its aqueous solution under acidic conditions (see the specifications of Japanese Patent Publication Sho-60-992 and U.S. Pat. No. 4,151,374).

Also known are 2'-deoxycoformycin (another name; pentostatin) and 2'-chloropentostatin as analogous compounds of coformycin which have the same molecular skeleton as that of coformycin [see, for example, U.S. Pat. No. 4,713,372, German Patent No. 2,517,596, "J. Org. Chem." 50, pp.1651–1656(1985) and "The Journal of Antibiotics" Vol.XXXVIII, No. 10, pp.1344–1349 (Oct. 1985)].

These coformycin analogues are known to have the activities inhibitory to adenosine deaminase, and on the basis of this property they have antitumor activities, or have such biological activities that when they are co-currently used as antitumor agents or antiviral agents, they can maintain and enhance the actions of the other antitumor agents or antiviral agents [see, for example, Spiers et al.'s report "Remissions in hairy cell leukemia with pentostatin (2'-deoxycoformycin)" [New Engl. J. Med., 316, pp.825–830 (1987)]; Daenen et al's report "Successful chemotherapy with deoxycoformycin in adult T-cell lymphoma-leukemia" [Brit. J. Haematol., 58, p. 723(1984)]; Yamaguchi et al.'s report "Clinical consequences of 2'-deoxycoformycin treatment in patients with refractory adult T-cell leukemia" [Leukemia Res., 10, pp.989–993(1986)]; Cass et al.'s report "Enhancement of 9-β-D-arabinofuranosyladenine cytotoxicity to mouse leukemia L1210 in vitro by 2'-deoxycoformycin" [Cancer Res., 36, pp.1486–1491 (1976)]; Wilson et al.'s report "Purinogenic immunodeficiency disease; Differential effects of deoxyadenosine and deoxyguanosine on DNA synthesis in human T lymphoblasts)"[J. Clin. Invest., 64, pp.1475–1484(1979)]; and Hershfield et al.'s report "Apparent suicide inactivation of human lymphoblast S-adenosylhomocysteine hydrolase by 2'-deoxyadenosine and adenine arabinoside: A basis for direct toxic effects of analogs of adenosine" [J. Biol. Chem., 254, pp.22–25 (1979)].

In particular, 2'-deoxycoformycin(another name; pentostatin) shows a strong activity inhibitory to adenosine deaminase and thus has an action to inhibit specifically lymphocytic cells containing a substantial amount of adenosine deaminase, so that it has been tried to use as a therapeutic agent in treatments of acute lymphocytic leukemias and adult T-cell leukemias [see, "Therapeutics" 22, No. 2, pp.71–75(1989) and "Antiviral Agents" written by Onodera et al. pp.194–195, published by Gakkai Shuppan Center, on Feb. 20, 1991, First Edition).

It is also known, however, that coformycin and its analogues already known and referred to above are unstable in their acidic aqueous solutions and are of fairly high acute toxicity on mammals, so that they are often disadvantageous in their practical applications as medicines.

Consequently, earnest desire at present is to provide novel coformycin derivatives which possess strong enzyme-inhibitory activities against adenosine deaminase and are stable in acidic aqueous solutions and are of low toxicity.

In the meanwhile, we, the present inventors, have already succeeded in synthesizing 7-O-(2,6-dideoxy-2-fluoro-α-L-talopyranosyl)daunomycinone or -adriamycinone which have antitumor activities, and also found that these 2'-fluoro-anthracycline derivatives have a higher stability in acidic aqueous solutions and a higher anti-tumor activity than those of the corresponding 2'-iodo, 2'-bromo or 2'-chloro-anthracycline derivatives (see, Japanese Patent Application First-Publication KOKAI Sho-62-145097 and European Patent Application First-Publication No. 230,013A1). It is assumed that such superior properties of 2'-fluoro-anthracyline derivatives as above-mentioned are attributable to the 2'-fluoro substituent of the sugar moiety having a high electro-negativity. We have further had many experiences and findings on the synthesis of a variety of 2-fluoro-sugars in connection with the synthesis of 2'-fluoro-anthracyline derivatives above-mentioned.

Coformycin is a compound represented by the following formula(A):

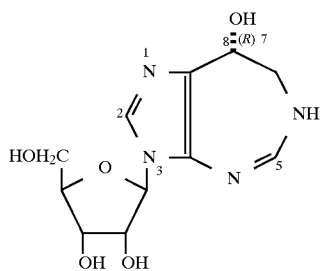

(A)

which is chemically named as (8R)-3-(β-D-ribofuranosyl)-3,6,7,8-tetrahydroimidazo[4,5-d][1,3]diazepin-8-ol. Coformycin may be synthesized starting from 9-β-D-ribofuranosylpurine [see, Japanese Patent Publication Sho-52-958 and "J.A.C.S." 96, p.4326(1974)].

As another method for the synthesis of coformycin, there is also a known process of producing coformycin in which 5-amino-1-(2,3,5-tri-O-acetyl-β-D-ribofuranosyl)-imidazole-4-carboxylic acid is used as the starting material, and is processed by multi-stage reactions to form an intermediate, 3-(β-D-ribofuranosyl)-6,7-dihydroimidazo[4,5-d][1,3]diazepin-8(3H)-one, followed by reducing the latter intermediate [see, H. J. Thomas et al.; "Nucleosides & Nucleotides" 5, No. 4, pp.431–439 (1986)]

DISCLOSURE OF INVENTION

In the light of our experience obtained in our invention relating to 7-O-(2,6-dideoxy-2-fluoro-α-L-talopyranosyl)daunomycinone and -adriamycinone, as well as our invention relating to 14-O-acyl derivatives of 7-O-(2,6-dideoxy-2-fluoro-α-L-talopyranosyl)adriamycinone (see the specifications of Japanese Patent Application Sho-61-288993 and the corresponding European Patent Application First-Publication No. 275,431A1), we had an expectation that if 2'-deoxy-2'-fluorocoformycin which corresponds to coformycin whose 2'-hydroxyl group has been replaced by a fluoro group can be synthesized, the resulting 2'-deoxy-2'-fluorocoformycin will have an enhanced stability in its acidic aqueous solution and also possesses an enzyme-inhibitory activity against adenosine deaminase.

Based on this expectation, we have further investigated extensively with the intention of synthesizing 2'-deoxy-2'-fluorocoformycin. As a result, we have first synthesized novel compounds, 3,5-di-O-benzoyl-2-deoxy-2-fluoro-α- and -β-D-ribofuranosyl bromides, from which we have successfully synthesized 2'-deoxy-2'-fluorocoformycin represented by the following formula(B)

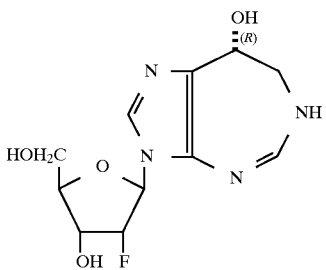

(B)

through a series of reaction steps, and then successfully synthesized 2'-deoxy-8-epi-2'-fluorocoformycin represented by the following formula(C)

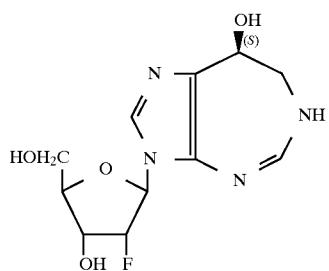

(C)

as a second product.

In addition, we have succeeded in synthesizing 2'-deoxy-2'-epi-2'-fluorocoformycin represented by the following formula(D)

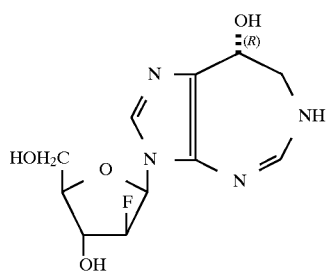

(D)

and 2'-deoxy-8,2'-diepi-2'-fluorocoformycin represented by the following formula(E)

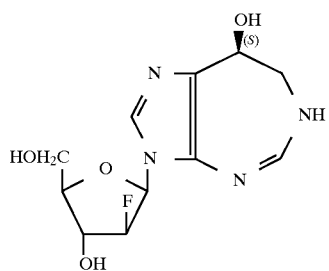

(E)

through a series of reaction steps with starting from a known compound, 3,5-di-O-benzoyl-2-deoxy-2-fluoro-α-D-arabinofuranosyl bromide. These four 2'-fluoro derivatives of coformycin as represented by the above formulae(B), (C), (D) and (E) have been confirmed to be novel compounds and to have strong enzyme-inhibitory activities against adenosine deaminase. Further, it is believed that these novel compounds will be able to remit the conditions of acute lymphocytic leukemias by administering them to patients due to their strong adenosine deaminase-inhibiting activities.

According to a first aspect of this invention, therefore, there is provided a compound selected from the group consisting of 2'-deoxy-2'-fluorocoformycin and 2'-deoxy-8-epi-2'-fluorocoformycin which are represented by the following general formula (Ia)

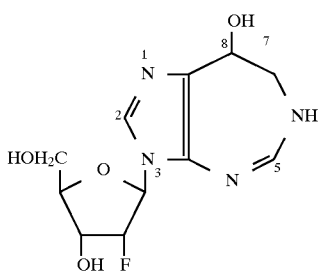

(Ia)

wherein the hydroxyl group at the 8-position has (R) or (S)-configuration, 2'-deoxy-2'-fluorocoformycin being the compound of the above formula where the 8-hydroxyl group has the (R)-configuration, while 2'-deoxy-8-epi-2'-fluorocoformycin being the compound of the above formula where the 8-hydroxyl group has the (S)-configuration.

According to a second aspect of this invention, there is further provided a compound selected from-the group consisting of 2'-deoxy-2'-epi-2'-fluorocoformycin and 2'-deoxy-8,2'-diepi-2'-fluorocoformycin which are represented by the following general formula (Ib)

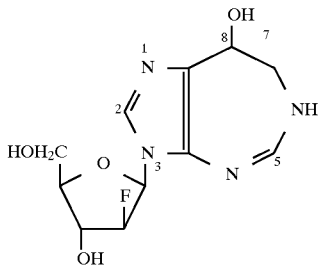

(Ib)

wherein the hydroxyl group at the 8-position has (R) or (S)-configuration, 2'-deoxy-2'-epi-2'-fluorocoformycin being the compound of the above formula where the 8-hydroxyl group has the (R)-configuration, while 2'-deoxy-8,2'-diepi-2'-fluorocoformycin being the compound of the above formula where the 8-hydroxyl group has the (S)-configuration.

2'-Deoxy-2'-fluorocoformycin according to the first aspect of this invention is a colorless solid and has a specific rotation $[\alpha]_D^{22}+12°$ (c 0.1, water). This substance has an enzyme-inhibitory activity against adenosine deaminase and also an antitumor activity.

2'-Deoxy-8-epi-2'-fluorocoformycin according to the first aspect of this invention is similarly a colorless solid and has a specific rotation $[\alpha]_D^{22}-115°$ (c 0.09, water). This substance has an enzyme-inhibitory activity against adenosine deaminase and also an antitumor activity.

2'-Deoxy-2'-epi-2'-fluorocoformycin according to the second aspect of this invention is a colorless solid and has a specific rotation $[\alpha]_D^{27}+118°$ (c 0.05, water). This substance has an enzyme-inhibitory activity against adenosine deaminase and also an antitumor activity.

2'-Deoxy-8,2'-diepi-2'-fluorocoformycin according to the second aspect of this invention is similarly a colorless solid and has a specific rotation $[\alpha]_D^{27}-27°$ (c 0.1, water). This substance has an enzyme-inhibitory activity against adenosine deaminase and also an antitumor activity.

The following are Test Examples in which some properties of the substances of formulae (Ia) and (Ib), respectively, according to the first and second aspects of this invention were examined.

TEST EXAMPLE 1

In this Example, the enzyme-inhibitory activity against adenosine deaminase of each of the following four compounds was evaluated by determining the concentration of each compound which can exert 50% inhibition of the activity of adenosine deaminase (namely, $IC_{50}$), for demonstrating that these compounds exhibit such enzyme-inhibiting activities:

2'-Deoxy-2'-fluorocoformycin (abbreviated as FCF);

2'-Deoxy-8-epi-2'-fluorocoformycin (abbreviated as e-FCF);

2'-Deoxy-2'-epi-2'-fluorocoformycin (abbreviated as Ara-FCF);

2'-Deoxy-8,2'-diepi-2'-fluorocoformycin (abbreviated as Ara-e-FCF).

The test of evaluating the inhibitory activity of each of the compounds against adenosine deaminase was carried out as given below.

A phosphate buffer solution (0.05M, pH 7.4), the compound to be tested and adenosine deaminase (3.85 units/l as a whole) (EC3.5.4.4, Type VI, a product of Sigma Chemical) were mixed together and the resulting mixture was allowed to stand at 25° C. for 5 minutes for pre-incubation, followed by adding adenosine (0.0561 μmol.) thereto to give a mixture of total volume of 1.50 ml. Optical density of the reaction mixture obtained was measured with time (measured at the wave length of 265 nm), and the $IC_{50}$ value of the tested compound against adenosine deaminase was calculated on the basis of decreases in the measured values of the optical density.

For the purpose of comparison, coformycin and pentostatin each were tested in the same manner as above.

The results of the tests above-mentioned are summarized in the following TABLE 1.

TABLE 1

| Compound tested (Abbreviation) | Enzyme-inhibitory activity, $IC_{50}$ (M) |
|---|---|
| 2'-Deoxy-2'-fluorocoformycin (FCF) | $1.7 \times 10^{-8}$ |
| 2'-Deoxy-8-epi-2'-fluorocoformycin (e-FCF) | $1.0 \times 10^{-7}$ |
| 2'-Deoxy-2'-epi-2'-fluorocoformycin (Ara-FCF) | $7.7 \times 10^{-10}$ |
| 2'-Deoxy-8,2'-diepi-2'-fluorocoformycin (Ara-e-FCF) | $2.2 \times 10^{-6}$ |
| Coformycin (Comparative) | $1.7 \times 10^{-9}$ |
| Pentostatin (Comparative) | $7.2 \times 10^{-10}$ |

TEST EXAMPLE 2

This Example illustrates that 2'-deoxy-2'-fluorocoformycin (FCF) and 2'-deoxy-2'-epi-2'-fluorocoformycin (Ara-FCF) are more stable than coformycin and pentostatin in aqueous hydrochloric acid-acidified solution (pH 2).

The test was carried out in accordance with the following method.

An aqueous solution (pH 2) of the test compound dissolved in water as acidified with hydrochloric acid was kept at 25° C., from which samples were taken out with time for analizing by thin-layer silica gel chromatography using acetonitrile-0.2M aqueous ammonium chloride (3:1) as the development solvent. The spot of the test compound on the silica gel thin-layer was detected by using UV method, staining tests with conc. sulfuric acid and coloring tests with aqueous ammonium molybdate sulfuric acid solution, in combination, whereby the time (in hour) required for the test compound to disappear completely in the aqueous hydrochloric acid solution was determined. By way of comparison, coformycin and pentostatin were also tested by the same method. The results are shown summarily in the following TABLE 2.

TABLE 2

| Abbreviation of test compound | Time (hours) required for complete disappearance of test compound in aqueous solution at pH 2 at 25° C. |
|---|---|
| FCF (This invention) | 15 |
| Ara-FCF (This invention) | 15 |
| Coformycin (Comparative) | 10 |
| Pentostatin (Comparative) | 1 |

TEST EXAMPLE 3

This Example shows that 2'-deoxy-2'-fluorocoformycin (FCF) and 2'-deoxy-8-epi-2'-fluorocoformycin (e-FCF) of formula (Ia) as well as 2'-deoxy-2'-epi-2'-fluorocoformycin (Ara-FCF) and 2'-deoxy-8,2'-diepi- 2'-fluorocoformycin (Ara-e-FCF) of formula (Ib) according to this invention have an action capable of making formycin A express an antibacterial activity against *Escherichia coli*. That is, from the following test it has been confirmed that formycin A, at a concentration of 100 mcg/ml, exhibited an antibacterial activity against *Escherichia coli* in the co-existence of the compounds of formulae (Ia) and (Ib) according to this invention, whereas formycin A, alone at that concentration, exhibits no antibacterial activity against *Escherichia coli*.

In this test, an aqueous solution of each of the compounds to be tested, i.e. FCF, e-FCF, Ara-FCF or Ara-e-FCF, at a concentration of 1 mcg/ml, was added in the form of several drops on the surface of a bouillon-agar medium containing formycin A at a concentration of 100 mcg/ml to form a circular film of the said aqueous solution thereon. Then, the medium was allowed to stand to make the test compound permeate into the bouillon-agar layer. Subsequently, a strain of *Escherichia coli* was inoculated on the overall surface of said medium and the inoculated medium was incubated at about 37° C. It was found that *Escherichia coli* was normally grown on the surface area of the medium except those areas where the test compound had been permeated, and where the bacteria could not grow to form the circular inhibition zone.

TEST EXAMPLE 4

This Example illustrates that 2'-deoxy-2'-epi-2'-fluorocoformycin (Ara-FCF) according to this invention is of lower toxicity in comparison with known adenosine deaminase inhibitors.

In tests for acute toxicity using mice as test animals, intraperitoneal administration of Ara-FCF did cause no death of the mice even at dose of 100 mg/kg.

In a similar acute toxicity test (by intravenous administration), coformycin was found to cause the death of mice by administration of 12.5 mg/kg of coformycin, and pentostatin was found to cause the decrease in the body weight of tested mice by administration of 25 mg/kg of pentostain (see Japanese Patent First-Publication KOKAI Sho-61/199797).

The compounds of formulae (Ia) and (Ib) according to this invention are useful as antitumor compounds which make use of their inhibitory activities against adenosine deaminase, or as compounds capable of maintaining and/or increasing activities of such certain antitumor agents or antiviral agents which are susceptible to action of adenosine deaminase. Also, the compounds of formulae (Ia) and (Ib) according to this invention are useful as supplementary agents for antibacterial compounds which are influenced by action of adenosine deaminase. In addition, the compounds of formulae (Ia) and (Ib) according to this invention are useful as such reagents to be used for analyzing the nucleic acid metabolism and for analyzing the etiological factors which participate in the nucleic acid metabolism, because of their stable activities for inhibiting adenosine deaminase.

Now, a process for the synthesis of 2'-deoxy-2'-fluorocoformycin and 2'-deoxy-8-epi-2'-fluorocoformycin represented by general formula (Ia) according to the first aspect of this invention is illustrated by referring to the following SYNTHETIC PROCESS CHART (A) which briefly depicts step 1 to step 19 of said synthetic process with starting from methyl 3-deoxy-3-fluoro-β-D-allopyranoside [compound (1)].

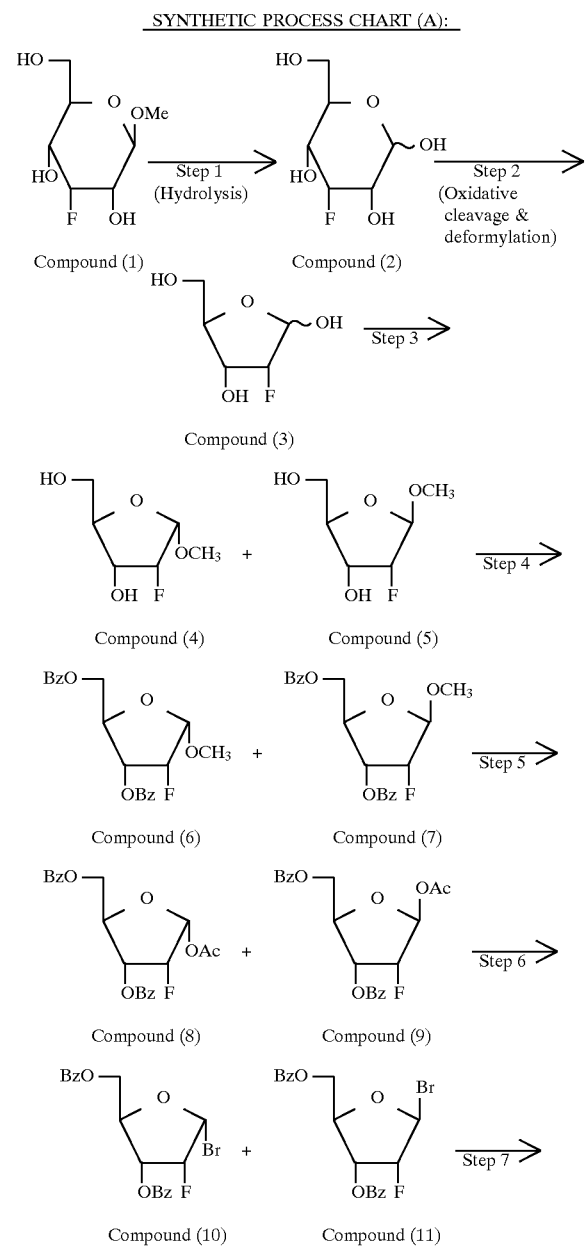

-continued
SYNTHETIC PROCESS CHART (A):
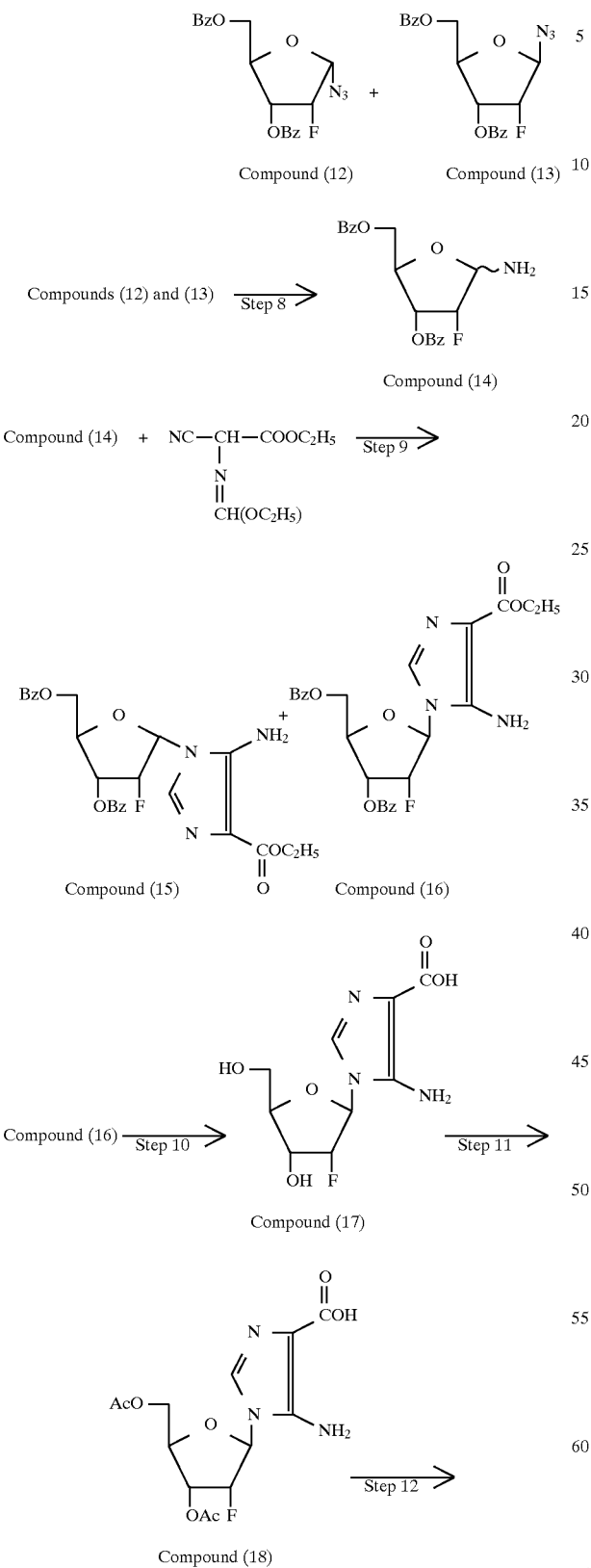
-continued
SYNTHETIC PROCESS CHART (A):
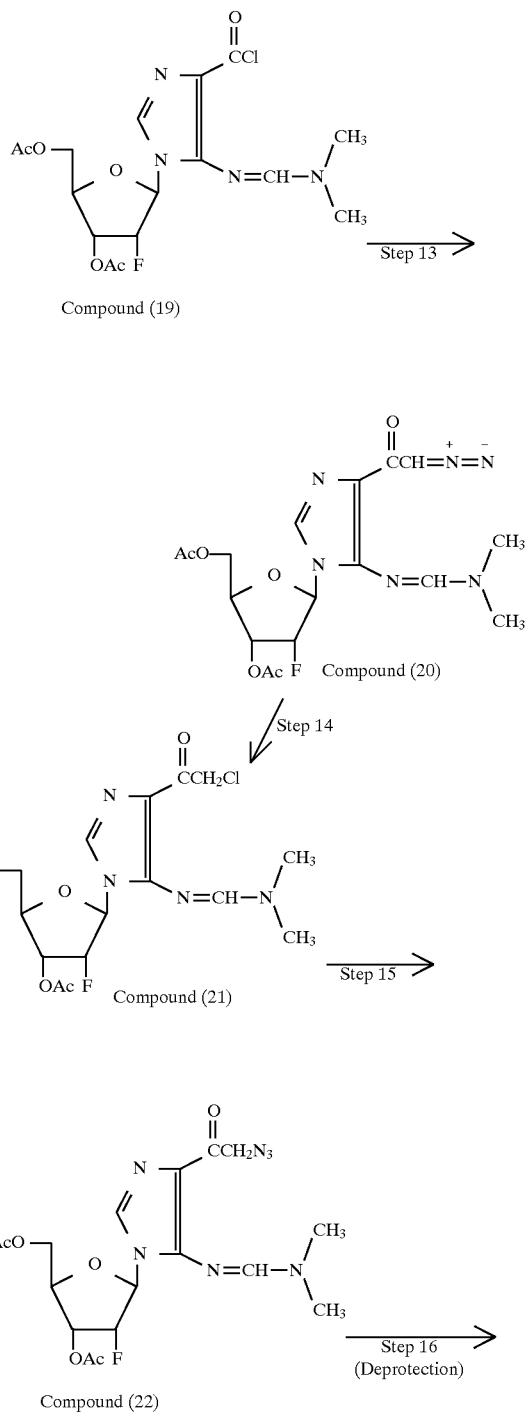

-continued
SYNTHETIC PROCESS CHART (A):

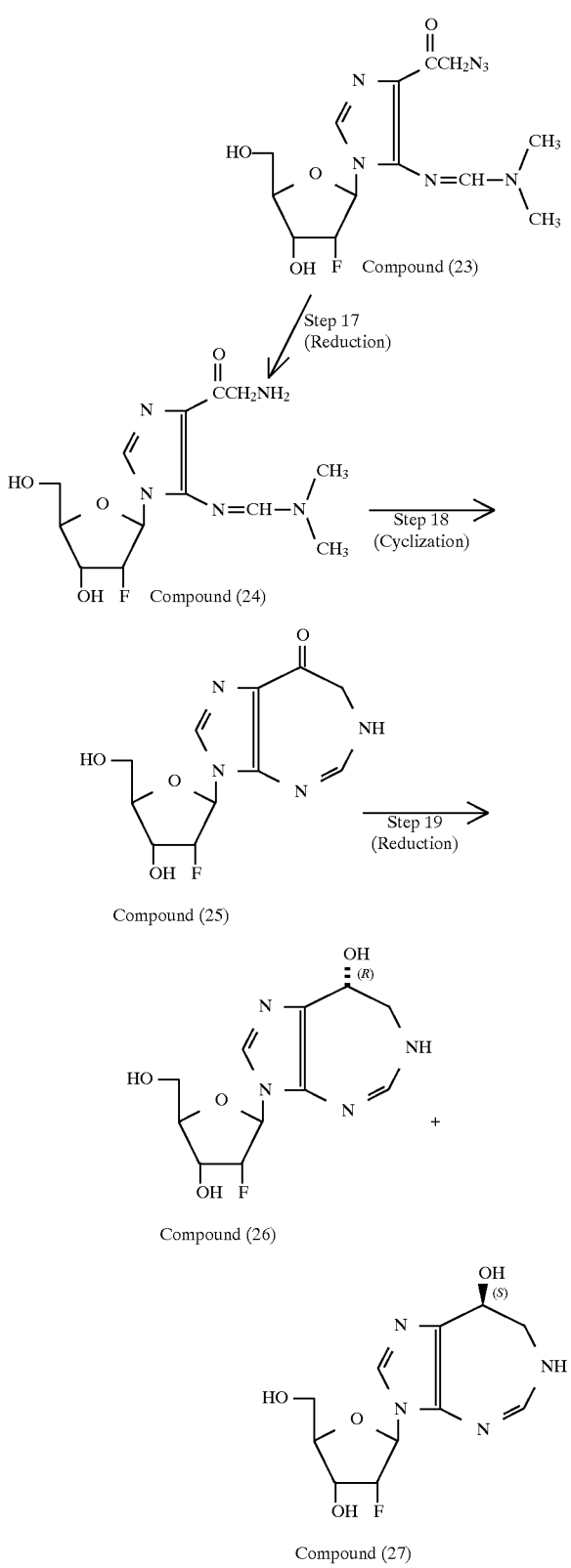

In SYNTHETIC PROCESS CHART (A), Me represents methyl group, Bz represents benzoyl group, and Ac represents acetyl group.

Respective reactions carried out in the steps 1-19 shown in SYNTHETIC PROCESS CHART (A) above are now explained.

In step 1, compound (1) known and used as the starting material, i.e. methyl 3-deoxy-3-fluoro-β-D-allopyranoside, is hydrolyzed in an aqueous hydrochloric acid solution under heating to eliminate the 1-methyl group, thus forming compound (2), i.e. 3-deoxy-3-fluoro-D-allopyranose.

In step 2, compound (2) obtained in step 1 above is dissolved in acetic acid and oxidized with lead tetra-acetate at room temperature to cause an oxidative cleavage of the α-glycol of 3-deoxy-3-fluoro-D-allopyranose, whereby the 2-carbon atom forms a formyl group. Thus, 2-deoxy-2-fluoro-4-O-formyl-D-ribose is formed as the oxidative product, which is then heated at 70°–90° C. in an aqueous solution under an acidic condition for the elimination of O-formyl group, whereby a ring-closing reaction occurs again to form 2-deoxy-2-fluoro-α,β-D-ribofuranose [compound (3)]. In the next step 3, compound (3) above is reacted with methanol in hydrogen chloride-methanol at room temperature for methylglycosidation, whereby forming a mixture of methyl 2-deoxy-2-fluoro-α-D-ribofuranoside [compound (4)] and methyl 2-deoxy-2-fluoro-β-D-ribofuranoside [compound (5)].

In step 4, the mixture of compound (4) and compound (5) obtained in step 3 is reacted, in pyridine at room temperature, with such an amount of benzoyl chloride as required to protect both the 3- and 5-hydroxyl groups of compounds (4) and (5) with benzoyl group. Thus, a mixture of methyl 3,5-di-O-benzoyl-2-deoxy-2-fluoro-α-D-ribofuranoside [compound (6)] and β-isomer thereof [compound (7)] is obtained. In step 5, the mixture of compounds (6) and (7) is acetylated with acetic anhydride in acetic acid in the presence of sulfuric acid at room temperature to replace the 1-methoxyl group on both of compounds (6) and (7) with an acetoxyl group, whereby a mixture of 3,5-di-O-benzoyl-2-deoxy-2-fluoro-α-D-ribofuranosyl acetate [compound (8)] and β-isomer thereof [compound (9)] is obtained.

In step 6, the mixture of compounds (8) and (9) is reacted with hydrogen bromide in a chlorinated hydrocarbon solvent, e.g. dichloromethane in the presence of acetic acid at room temperature to replace the 1-acetoxyl group of both of compounds (8) and (9) by a bromo group, whereby a mixture of 3,5-di-O-benzoyl-2-deoxy-2-fluoro-α-D-ribofuranosyl bromide [compound (10)] and β-isomer thereof [compound (11)] is obtained.

In step 7, the mixture of compounds (10) and (11) is reacted with an alkali metal azide, e.g. sodium azide in acetonitrile or any other suitable organic solvent in the presence of tetraethylammonium bromide at room temperature, to replace the 1-bromo group of both of compounds (10) and (11) by azido group, whereby a mixture of 3,5-di-O-benzoyl-2-deoxy-2-fluoro-α-D-ribofuranosyl azide [compound (12)] and β-isomer thereof [compound (13)] is obtained.

In step 8, the mixture of compounds (12) and (13) obtained in step 7 is reacted with hydrogen in dioxane in the presence of a hydrogenation catalyst, e.g. palladium black at room temperature and thus is catalytically reduced, in order to effect the reduction into amino group of the azido group of the azide compounds (12) and (13), whereby 3,5-di-O-benzoyl-2-deoxy-2-fluoro-α,β-D-ribofuranosyl amine [compound (14)] is produced.

In step 9, compound (14) is reacted with ethyl N-(α-cyano-α-ethoxycarbonylmethyl)formimidate represented by the following formula $$\begin{array}{c} NC-CH-COOC_2H_5 \\ | \\ N=CH(OC_2H_5) \end{array}$$

[which may be prepared according to the method described by D. H. Robinson et al.; "J. C. S. Perkin I" p.1715 (1972)] in a chlorinated hydrocarbon solvent, e.g. dichloroethane, under heating and refluxing, in order to convert the 1-amino group of compound (14) into 5-amino-4-ethoxycarbonyl-1-imidazolyl group. This reaction may be carried out in accordance with the method proposed by G. Mackenzie et al. in "J. C. S. Chem. Comm.", pp.453–455 (1976). This reaction results in the formation of a mixture of ethyl ester of 5-amino-1-(3,5-di-O-benzoyl-2-deoxy-2-fluoro-β-D-ribofuranosyl)imidazole-4-carboxylic acid [compound (16)] and α-isomer thereof [compound (15)]. This mixture may be subjected to silica gel column chromatography (using ethyl acetate-chloroform as development solvent) to isolate the above β-isomer compound (16).

In step 10, compound (16) isolated in step 9 is treated with sodium hydroxide in aqueous dioxane under heating to effect the elimination of the benzoyl group and the ester-forming ethyl group therefrom, whereby 5-amino-1-(2-deoxy-2-fluoro-β-D-ribofuranosyl)imidazole-4-carboxylic acid [compound (17)] is obtained.

In step 11, compound (17) is suspended in pyridine and reacted with acetic anhydride at room temperature for the protection of the hydroxyl groups of the sugar moiety of compound (17) with acetyl groups, whereby 5-amino-1-(3,5-di-O-acetyl-2-deoxy-2-fluoro-β-D-ribofuranosyl)imidazole-4-carboxylic acid [compound (18)] is produced.

In step 12, compound (18) is dissolved in tetrahydrofuran and reacted with N,N-dimethylchloroforminium chloride under ice-cooling, whereby 1-(3,5-di-O-acetyl-2-deoxy-2-fluoro-β-D-ribofuranosyl)-5-(dimethylaminomethyleneamino)imidazole-4-carbonyl chloride [compound (19)] is produced.

In step 13, compound (19) is reacted with diazomethane at room temperature without being separated from the reaction solution, so that the 4-chlorocarbonyl group of compound (19) is converted into diazoacetyl group, affording 1-(3,5-di-O-acetyl-2-deoxy-2-fluoro-β-D-ribofuranosyl)-4-diazoacetyl-5-(dimethylaminomethyleneamino)-imidazole [compound (20)].

In step 14, compound (20) is reacted in dichloromethane with hydrogen chloride in the form of a diethylether solution under ice-cooling, to convert the 4-diazoacetyl group of compound (20) into 4-chloroacetyl group. Thereby, 1-(3,5-di-O-acetyl-2-deoxy-2-fluoro-β-D-ribofuranosyl)-4-chloroacetyl-5-(dimethylaminomethyleneamino)imidazole [compound (21)] is produced.

In step 15, compound (21) is reacted with sodium azide in N,N-dimethylformamide at room temperature for converting the chloro group of compound (21) into azido group, whereby 1-(3,5-di-O-acetyl-2-deoxy-2-fluoro-β-D-ribofuranosyl)-4-azidoacetyl-5-(dimethylaminomethyleneamino)imidazole [compound (22)] is produced.

In step 16, compound (22) is dissolved in methanol and treated with a methanolic solution of sodium methylate for removing the acetyl groups from the acetyl-protected hydroxyl groups of the sugar moiety of compound (22). Thereby, 4-azidoacetyl-1-(2-deoxy-2-fluoro-β-D-ribofuranosyl)-5-(dimethylaminomethyleneamino) imidazole [compound (23)] is produced.

In step 17, compound (22) is subjected to catalytic reduction with hydrogen in the presence of a hydrogenation catalyst, e.g. palladium black in methanol at room temperature for converting the azido group of compound (22) into amino group. Thereby, 4-aminoacetyl-1-(2-deoxy-2-fluoro-β-D-ribofuranosyl)-5-(dimethylaminomethyleneamino) imidazole [compound (24)] is produced.

In step 18, compound (24) is dissolved in methanol and treated with a methanolic solution of sodium methylate at room temperature to effect the ring-formation of the substituents on the imidazole ring of compound (24). Thus, 3-(2-deoxy-2-fluoro-β-D-ribofuranosyl)-6,7-dihydroimidazo-[4,5-d] [1,3]diazepin-8(3H)-one [compound (25)] is produced.

In step 19, compound (25) is dissolved in aqueous methanol and reduced with sodium borohydride at room temperature so that the 8-ketone group on the diazepine ring of compound (25) is converted into hydroxyl group by reduction. Thus, (8R)-3-(2-deoxy-2-fluoro-β-D-ribofuranosyl)-3,6,7,8-tetrahydroimidazo[4,5-d][1,3]diazepin-8-ol, namely 2'-deoxy-2'-fluorocoformycin [compound (26)] and (8S)-3-(2-deoxy-2-fluoro-β-D-ribofuranosyl)-3,6,7,8-tetrahydroimidazo[4,5-d][1,3]diazepin-8-ol, namely 2'-deoxy-8-epi-2'-fluorocoformycin [compound (27)] are synthesized as the final desired products.

Further, a process for the synthesis of 2'-deoxy-2'-epi-2'-fluorocoformycin and 2'-deoky-8,2'-diepi-2'-fluorocoformycin represented by general formula (Ib) according to the second aspect of this invention is illustrated by referring to the following SYNTHETIC PROCESS CHART (B) which briefly depicts step a to step m of said synthetic process with starting from 3,5-di-O-benzoyl-2-deoxy-2-fluoro-α-D-arabinofuranosyl bromide [compound (28)]. In this SYNTHETIC PROCESS CHART (B), too, Bz represents benzoyl group and Ac represents acetyl group.

SYNTHETIC PROCESS CHART (B):

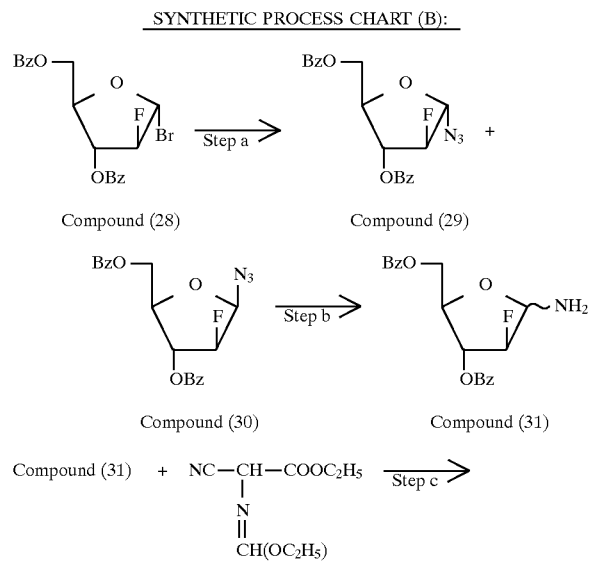

-continued
SYNTHETIC PROCESS CHART (B):
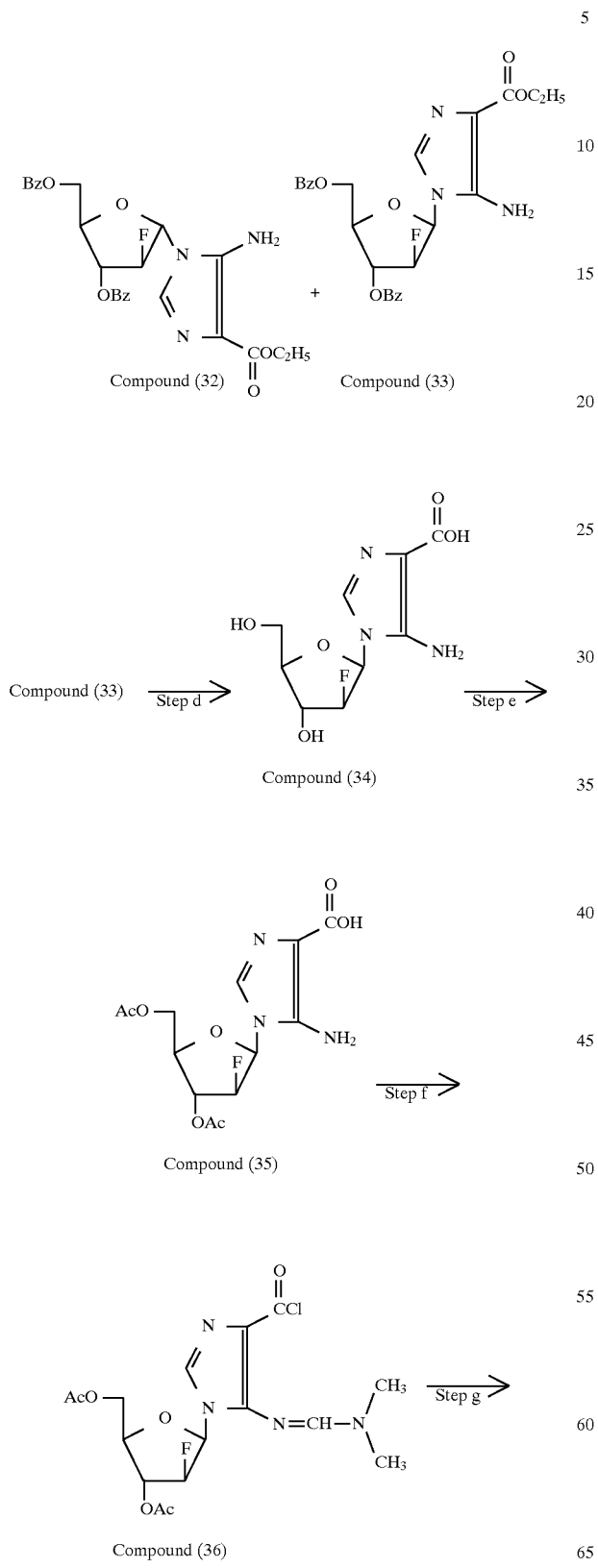
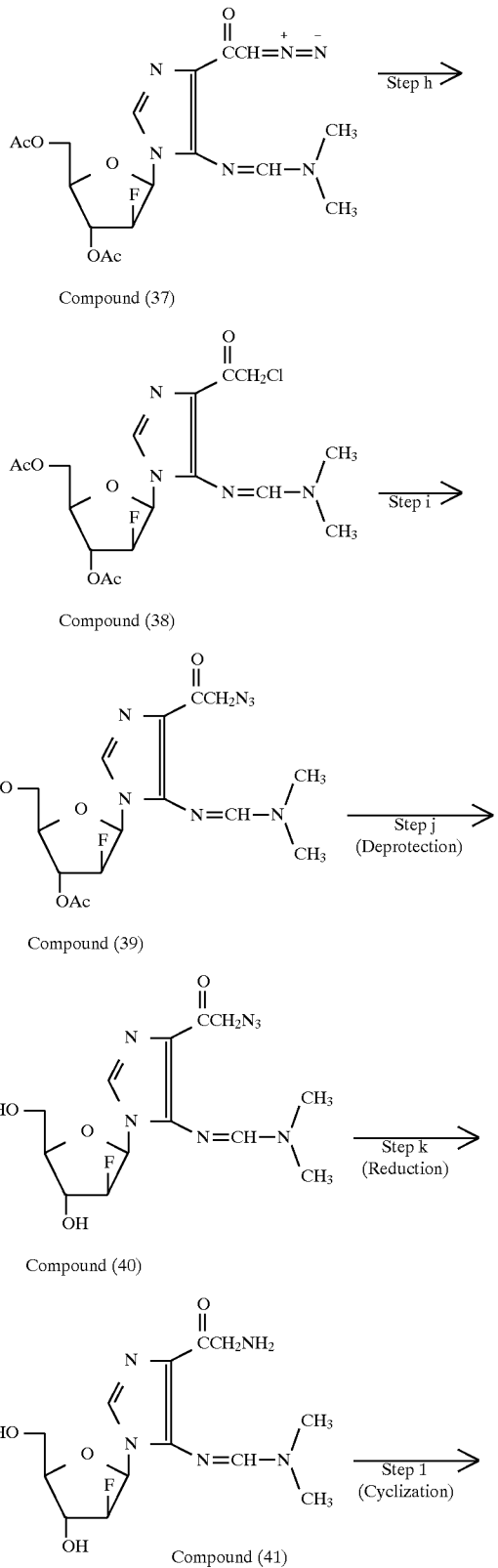

-continued
SYNTHETIC PROCESS CHART (B):

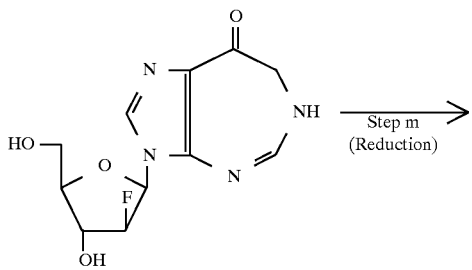

Compound (42)

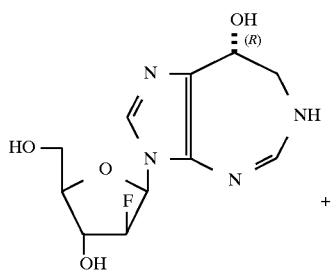

Compound (43)

+

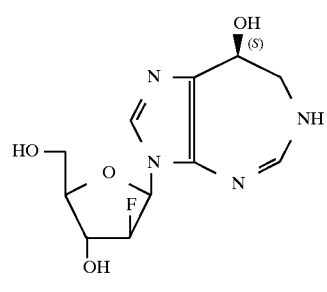

Compound (44)

Respective reactions to be carried out in step a to step m shown in SYNTHETIC PROCESS CHART (B) are now explained.

In step a, compound (28) already known and to be used as the starting material in this process, i.e. 3,5-di-O-benzoyl-2-deoxy-2-fluoro-α-D-arabinofuranosyl bromide, is reacted with sodium azide for replacing the 1-bromo group of compound (28) with azido group. This step a may be carried out in a similar manner to the step 7 of SYNTHETIC PROCESS CHART (A). Thus, a mixture of 3,5-di-O-benzoyl-2-deoxy-2-fluoro-α-D-arabinofuranosyl azide [compound (29)] and β-isomer thereof [compound (30)] is obtained.

In step b, the azido group of each of azide compounds (29) and (30) obtained in step a is reduced to amino group. For this purpose, step b involves the catalytic reduction of the mixture of compounds (29) and (30) with hydrogen in dioxane in the presence of a hydrogenation catalyst, e.g. palladium black at room temperature in the same manner as in the step 8 of SYNTHETIC PROCESS CHART (A). Thus, 3,5-di-O-benzoyl-2-deoxy-2-fluoro-α,β-D-arabinofuranosyl amine [compound (31)] is obtained.

In step c, compound (31) is reacted with ethyl N-(α-cyano-α-ethoxycarbonylmethyl)formimidate represented by the following formula

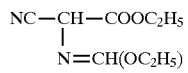

in a chlorinated hydrocarbon solvent, e.g. dichloroethane under heating and refluxing to convert the 1-amino group of compound (31-) into 5-amino-4-ethoxycarbonyl-1-imidazolyl group. This reaction may be effected in the same manner as in the step 9 of SYNTHETIC PROCESS CHART (A).

By this reaction, ethyl 5-amino-1-(3,5-di-O-benzoyl-2-deoxy-2-fluoro-β-D-arabinofuranosyl)imidazole-4-carboxylate [compound (33)] and its α-isomer [compound (32)] are obtained as a mixture. β-Isomer compound (33) may be isolated by subjecting the mixture to silica gel column chromatography (using ethyl acetate-chloroform as a development solvent).

In step d, compound (33) as isolated in step c is treated with sodium hydroxide in aqueous dioxane under heating for removing the benzoyl groups and the ester-forming ethyl group from compound (33). This treatment may be carried out in the same manner as in the step 10 in SYNTHETIC PROCESS CHART (A). Thus, 5-amino-1-(2-deoxy-2-fluoro-β-D-arabinofuranosyl)imidazole-4-carboxylic acid [compound (34)] is obtained.

In step e, compound (34) is suspended in pyridine and reacted with acetic anhydride at room temperature for protecting the hydroxyl groups of the sugar moiety of compound (34) with acetyl groups. This acetylation reaction may be effected in the same manner as in the step 11 of SYNTHETIC PROCESS CHART (A). Thus, 5-amino-1-(3,5-di-O-acetyl-2-deoxy-2-fluoro-β-D-arabinofuranosyl)imidazole-4-carboxylic acid [compound (35)] is produced.

In step f, compound (35) is dissolved in tetrahydrofuran and reacted with N,N-dimethylchloroforminium chloride under ice-cooling. This reaction may be carried out in the same manner as in the step 12 of SYNTHETIC PROCESS CHART (A). By this reaction, 1-(3,5-di-O-acetyl-2-deoxy-2-fluoro-β-D-arabinofuranosyl)-5-(dimethylaminomethyleneamino)imidazole-4-carbonyl chloride [compound(36)] is produced.

In step g, compound (36) produced in step f is directly, i.e. without being separated from the reaction solution, reacted with diazomethane at room temperature. This reaction may be effected in the same manner as in the step 13 of SYNTHETIC PROCESS CHART (A). By this reaction, the 4-chlorocarbonyl group of compound (36) is converted into diazoacetyl group, thus affording 1-(3,5-di-O-acetyl-2-deoxy-2-fluoro-β-D-arabinofuranosyl)-4-diazoacetyl-5-(dimethylaminomethyleneamino)imidazole [compound (37)].

In step h, compound (37) is dissolved in dichloromethane and is reacted with a solution of hydrogen chloride in diethylether under ice-cooling, whereby converting the 4-diazoacetyl group of compound (37) into 4-chloroacetyl group. This conversion reaction may be conducted in the same manner as in the step 14 of SYNTHETIC PROCESS CHART (A). By this reaction for the conversion of the 4-diazoacetyl group into-4-chloroacetyl group, there is produced 1-(3,5-di-O-acetyl-2-deoxy-2-fluoro-β-D-arabinofuranosyl)-4-chloroacetyl-5-(dimethylaminomethyleneamino)imidazole [compound (38)].

In step i, compound (38) is reacted with sodium azide in N,N-dimethylformamide at room temperature for converting the chloro group of compound (38) into azido group. This reaction may be conducted in the same manner as in the step 15 of SYNTHETIC PROCESS CHART (A). By this reaction, 1-(3,5-di-O-acetyl-2-deoxy-2-fluoro-β-D-arabinofuranosyl)-4-azidoacetyl-5-(dimethylaminomethyleneamino)imidazole [compound (39)] is produced.

In step j, compound (39) is dissolved in methanol and then treated with a methanolic solution of sodium methylate for removing therefrom the acetyl groups which protect the hydroxyl groups of the sugar moiety of compound (39). This reaction may be conducted in the same manner as in the step 16 of SYNTHETIC PROCESS CHART (A). By this reaction, 4-azidoacetyl-1-(2-deoxy-2-fluoro-β-D-arabinofuranosyl)-5-(dimethylaminomethyleneamino) imidazole [compound (40)] is produced.

In step k, compound (40) is catalytically reduced with hydrogen in the presence of a hydrogenation catalyst, e.g. palladium black, in methanol at room temperature for converting the azido group of compound (40) into amino group. This reduction may be conducted in the same manner as in the step 17 of SYNTHETIC PROCESS CHART (A). By this reaction, 4-aminoacetyl-1-(2-deoxy-2-fluoro-β-D-arabinofuranosyl)-5-(dimethylaminomethyleneamino) imidazole [compound (41)] is produced.

In step 1, compound (41) is dissolved in methanol and treated with a methanolic solution of sodium methylate at room temperature, whereby the cyclization of the substituents on the imidazole ring of compound (41) occurs. This ring-forming reaction may be conducted in the same manner as in the step 18 of SYNTHETIC PROCESS CHART (A). Thus, 3-(2-deoxy-2-fluoro-β-D-arabinofuranosyl)-6,7-dihydroimidazo[4,5.-d] [1,3]diazepin-8(3H)-one. [Compound (42)] is produced.

In step m, compound (42) is dissolved in aqueous methanol and reduced with sodium borohydride at room temperature. This reduction may be effected in the same manner as in the step 19 of SYNTHETIC PROCESS CHART (A). By this step, the 8-ketone group on the diazepine ring of compound (42) is reduced and converted into hydroxyl group. Thus, (8R)-3-(2-deoxy-2-fluoro-β-D-arabinofuranosyl)- 3,6,7,8-tetrahydroimidazo [4,5-d][ 1,3 ]diazepin-8-ol, namely 2'-deoxy-2'-epi-2'-fluorocoformycin [compound (43)] and (8S)-3-(2-deoxy-2-fluoro-β-D-arabinofuranosyl)-3,6,7,8-tetrahydroimidazo[4,5-d][1,3] diazepin-8-ol, namely 2'-deoxy-8,2'-diepi-2'-fluorocoformycin [compound (44)] are synthesized as the final desired products.

When each of 3,5-di-O-benzoyl-2-deoxy-2-fluoro-α-D-ribofuranosyl bromide [compound (10)] and 3,5-di-O-benzoyl-2-deoxy-2-fluoro-β-D-ribofuranosyl bromide [compound (11)], which are obtained as the intermediate products in the synthetic process shown in SYNTHETIC PROCESS CHART (A) above, is subjected to solvolysis in methanol in the presence of a catalytic amount of sodium methylate, the elimination of the benzoyl groups takes place, whereby 2-deoxy-2-fluoro-α- or -β-D-ribofuranosyl bromide is produced. The bromo group of the latter compound may be replaced by other halo group according to a conventional method.

These halo-sugars so obtained are novel compounds. Their O-protected derivatives as obtained by protecting the 3- and 5-hydroxyl groups with suitable hydroxyl-protecting groups, for example, acetyl or benzoyl group are useful as intermediates for the synthesis of 2'-deoxy-2'-fluorocoformycin or the 8-epi-isomer thereof which are represented by general formula(Ia) as previously mentioned.

The above-mentioned halo-sugars may be represented as 2-deoxy-2-fluoro-α- and -β-D-ribofuranosyl halides having the following general formula(II)

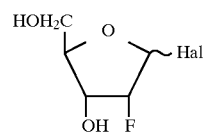

wherein Hal is a bromine, chlorine or iodine atom.

According to a third aspect of this invention, therefore, there is provided, as novel compound, a compound selected from 2-deoxy-2-fluoro-α- and -β-D-ribofuranosyl halides represented by general formula(II).

When each of 3,5-di-O-benzoyl-2-deoxy-2-fluoro-α-D-ribofuranosyl azide [compound (12)] and 3,5-di-O-benzoyl-2-deoxy-2-fluoro-β-D-ribofuranosyl azide [compound (13)], as well as 3,5-di-O-benzoyl-2-deoxy-2-fluoro-β-D-arabinofuranosyl azide [compound (29)] and 3,5-di-O-benzoyl-2-deoxy-2-fluoro-β-D-arabinofuranosyl azide [compound (30)], which are obtained as intermediates in the synthetic processes shown in SYNTHETIC PROCESS CHARTS (A) and (B), respectively, is subjected to solvolysis in methanol or aqueous dioxane in the presence of sodium methylate or sodium hydroxide, the elimination of benzoyl groups takes place therefrom. Thus, 2-deoxy-2-fluoro-α- and -β-D-ribofuranosyl azides, as well as 2-deoxy-2-fluoro-α- and -β-D-arabinofuranosyl azides are produced.

These four azido sugars are novel compounds. Their O-protected derivatives as obtained by protecting the 3- and 5-hydroxyl groups with suitable hydroxyl-protecting groups, for example, acetyl or benzoyl group are useful as intermediates for the synthesis of 2'-deoxy-2'-fluorocoformycin or the 8-epi-isomer thereof represented by general formula(Ia) or for the synthesis of 2'-deoxy-2'-epi-2'-fluorocoformycin or the 8-epi-isomer thereof represented by general formula(Ib), as previously mentioned.

The four azido sugars above-mentioned can be represented collectively as a compound selected from the group consisting of 2-deoxy-2-fluoro-α- and -β-D-ribofuranosyl azides and 2-deoxy-2-fluoro-α- and -β-D-arabinofuranosyl azides which are represented by the following general formula(III)

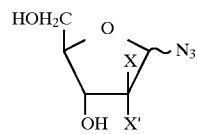

wherein X and X' are independently a hydrogen atom or a fluorine atom, 2-deoxy-2-fluoro-α- and -β-D-ribofuranosyl azides being the compounds of the above formula where X is a hydrogen atom and X' is a fluorine atom, while 2-deoxy-2-fluoro-α- and -β-D-arabinofuranosyl azides being the compounds of the above formula where X is a fluorine atom and X' is a hydrogen atom.

According to a fourth aspect of this invention, therefore, there is provided, as novel compound, a compound selected from the group consisting of 2-deoxy-2-fluoro-α- and -β-D-ribofuranosyl azides and 2-deoxy-2-fluoro-α- and -β-D-arabinofuranosyl azides which are represented by general formula(III).

The azido sugars of formula(III) have been found not to exhibit any antibacterial activity against bacteria at a concentration of 100 mcg/ml.

When each of 3,5-di-O-benzoyl-2-deoxy-2-fluoro-α, β-D-ribofuranosyl amine [compound (14)] and 3,5-di-O-benzoyl-2-deoxy-2-fluoro-α,β-D-arabinofuranosyl amine [compound (31)], which are obtained as intermediates in the synthetic processes shown in SYNTHETIC PROCESS CHARTS (A) and (B), respectively, is subjected to protection of the 1-amino group thereof and the subsequent removal of the benzoyl groups from the resulting N-protected product followed by the removal of the amino-protecting group by appropriate methods, there can be produced 2-deoxy-2-fluoro-α, β-D-ribofuranosyl amine and 2-deoxy-2-fluoro-α,β-D-arabinofuranosyl amine as novel compounds. These amino sugars can also be produced directly from 2-deoxy-2-fluoro-D-ribofuranosyl azide or 2-deoxy-2-fluoro-D-arabinofuranosyl azide of general formula (III) by catalytic reduction.

According to a fifth aspect of this invention, therefore, there is provided, as novel intermediate, a compound selected from the group consisting of 2-deoxy-2-fluoro-α, β-D-ribofuranosyl amine and 2-deoxy-2-fluoro-α,β-D-arabinofuranosyl amine which are represented by the following general formula (IV)

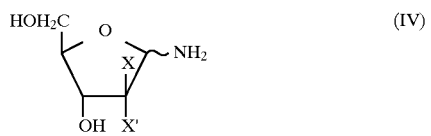

wherein X and X' are independently a hydrogen atom or a fluorine atom, 2-deoxy-2-fluoro-α,β-D-ribofuranosyl amine being the compound of the above formula where X is a hydrogen atom and X' is a fluorine atom, while 2-deoxy-2-fluoro-α,β-D-arabinofuranosyl amine being the compound of the above formula where X is a fluorine atom and X' is a hydrogen atom.

2-Deoxy-2-fluoro-α,β-D-ribofuranosyl amine and 2-deoxy-2-fluoro-α,β-D-arabinofuranosyl amine embraced by the compounds of general formula (IV) have been recognized to exhibit antibacterial activities against certain bacteria. That is, a test was conducted to measure the minimum growth-inhibitory concentrations (MIC, mcg/ml) of these compounds against some microorganisms using a standard serial dilution assay method. The test results are shown in the following Table.

TABLE 4

| | MIC (mcg/ml) | |
| --- | --- | --- |
| Test organism | 2-deoxy-2-fluoro-α,β-D-ribofurano-syl amine | 2-deoxy-2-fluoro-α,β-D-arabino-furanosyl amine |
| *Providencia rettgeri* GN466 | 50 | 50 |
| *Providencia* sp. 2991 | 100 | 100 |

Further, 5-amino-1-(2-deoxy-2-fluoro-β-D-ribofuranosyl)imidazole-4-carboxylic acid [compound (17)] and 5-amino-1-(2-deoxy-2-fluoro-β-D-arabinofuranosyl) imidazole-4-carboxylic acid [compound (34)], which are obtained as intermediates in the synthetic processes given in SYNTHETIC PROCESS CHARTS (A) and (B) above-mentioned, are novel compounds and are useful intermediates for the said synthetic processes.

According to a sixth aspect of this invention, therefore, there is provided as new intermediate product a compound selected from the group consisting of 5-amino-1-(2-deoxy-2-fluoro-β-D-ribofuranosyl) imidazole-4-carboxylic acid and 5-amino-1-(2-deoxy-2-fluoro-β-D-arabinofuranosyl)-imidazole-4-carboxylic acid which are represented by the following general formula (V)

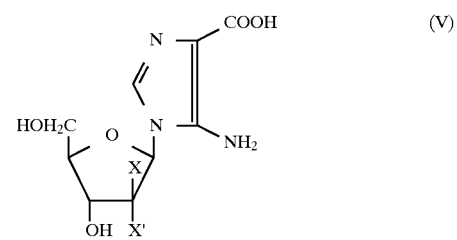

wherein X and X' are independently a hydrogen atom or a fluorine atom, 5-amino-1-(2-deoxy-2-fluoro-β-D-ribofuranosyl)imidazole-4-carboxylic acid being the compound of the above formula where X is a hydrogen atom and X' is a fluorine atom, while 5-amino-1-(2-deoxy-2-fluoro-β-D-arabinofuranosyl)imidazole-4-carboxylic acid being the compound of the above formula where X is a fluorine atom and X' is a hydrogen atom.

Furthermore, 3-(2-deoxy-2-fluoro-β-D-ribofuranosyl)-6,7-dihydroimidazo[4,5-d][1,3]diazepin-8(3H)-one [compound (25)] and 3-(2-deoxy-2-fluoro-β-D-arabinofuranosyl)-6,7-dihydroimidazo[4,5-d][1,3]diazepin-8(3H)-one [compound (42)], which are obtained as intermediates by the synthetic processes given in SYNTHETIC PROCESS CHARTS (A) and (B) above, are novel compounds. These compounds are useful intermediates in that when they are subjected to reduction, there can be produced the compounds of general formula (Ia) according to the first aspect of this invention or the compounds of general formula (Ib) according to the second aspect of this invention.

According to a seventh aspect of this invention, therefore, there is provided 3-(2-deoxy-2-fluoro-β-D-ribofuranosyl or -arabinofuranosyl)-6,7-dihydroimidazo-[4,5-d][1,3]diazepin-8(3H)-one represented by the following general formula (VI)

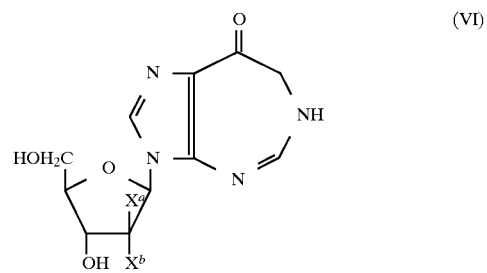

wherein $X^a$ is a hydrogen atom and $X^b$ is a fluorine atom, or $X^a$ is a fluorine atom and $X^b$ is a hydrogen atom.

BEST MODE FOR CARRYING OUT THE INVENTION

Now, this invention is concretely illustrated by making reference to EXAMPLES 1, 2 and 3, but is in no way limited thereto.

EXAMPLE 1

(1) Synthesis of 3-deoxy-3-fluoro-D-allopyranose [compound (2)] from methyl 3-deoxy-3-fluoro-β-D-allopyranoside [compound (1)]

Compound (1) → Step 1 → (Compound (2))

Methyl 3-deoxy-3-fluoro-β-D-allopyranoside (24.5 g) [compound (1); this compound is described in "J. Org. Chem.", 48, pp. 4734–4743 (1983) by Peter J. Card et al.] was dissolved in 6M hydrochloric acid (500 ml) and the solution was allowed to stand at 70° C. for 8 hours (for hydrolysis reaction). The resulting reaction solution was concentrated and the syrup so obtained was dissolved in water (400 ml). The solution was neutralized with addition of ion-exchange resin, Dowex 1×2(OH⁻ form) (100–200 mesh) (apparently 800 ml), then filtered and the filtrate was concentrated to afford the titled compound (2) (22.1 g) as a colorless syrup. Yield: 97%.

$^{19}$F-NMR Spectrum (in deutero-dimethylsulfoxide, internal standard: Freon 11):

δ −212.8 (ddd, J=30,33, 54 Hz), −215.3 (dt, J=32,32, 54 Hz).

This substance was crystallized from a mixture of methanol-chloroform, yielding colorless crystals; mp. 120.5–122.5° C.

Elemental Analysis:
Found: C 39.55%, H 6.09%, F 10.42%.
Calculated for $C_6H_{11}FO_5$: C 39.56%, H 6.09%, F 10.43%.

(2) Synthesis of methyl 2-deoxy-2-fluoro-α- and -β-D-ribofuranosides [compound (4) and compound (5)]

Compound (2) (15.2 g) obtained in item (1) above was dissolved in acetic acid (450 ml), to which lead tetra-acetate (38.8 g) was added, and the resulting mixture was kept at room temperature for 30 minutes to effect the reaction. Thus, oxidative cleavage of the α-glycol occurred. Then, water (80 ml) was added to the resulting reaction solution, and the mixture obtained was allowed to stand at 90° C. for 24 hours to effect the de-O-formylation. The resulting reaction solution containing 2-deoxy-2-fluoro-α,β-D-ribofuranose produced as compound (3) was concentrated and the resulting syrup was purified by silica gel column chromatography (developer; methanol-ethyl acetate, 1:5), affording a syrupy substance (12.6 g).

Subsequently, the syrup was dissoleved in 0.5M hydrogen chloride-methanol solution (260 ml) and the solution was allowed to stand at room temperature for 3 days to effect the methylglycosidation. The resulting reaction solution was neutralized with addition of ion-exchange resin, Dowex 1×2 (OH⁻ form) (100–200 mesh) and then filtered, and the filtrate was concentrated to yield a mixture of the titled compounds (4) and (5) [compounds (4): (5) at ratio of about 1:17] as a colorless solid (12.2 g). Yield: 88%.

The separation of compounds (4) and (5) was easily made by silica gel column chromatography (developer; ethyl acetate-toluene, 4:1), affording compound (4) (α-isomer) as a syrup, and compound (5) (β-isomer) as colorless needles.

Compound (4) (α-isomer):

$[\alpha]_D^{25}$ +149° (c 1, methanol);

$^1$H-NMR spectrum (in deutero-chloroform, TMS as internal standard):

δ 1.74 (1H, dd, OH-5), 2.72 (1H, dd, $J_{OH-3,F}$=2 Hz, OH-3), 3.51 (3H, s, OCH₃), 4.84 (1H, ddd, $J_{2,F}$=51 Hz, H-2), 5.07 (1H, d, $J_{1,2}$=4 Hz, H-1);

$^{19}$F-NMR spectrum (in deutero-chloroform, Freon 11 as internal standard):

δ −217.9 (slightly br d, J=51 Hz).

Elemental Analysis:
Found: C 43.06%, H 6.64%, F 11.46%.
Calculated for $C_6H_{11}FO_4$: C 43.37%, H 6.67%, F 11.44%.

Compound (5) (β-isomer):

mp. 85.5°–86.0° C. (measured after recrystallization from chloroform-n-hexane);

$[\alpha]_D^{24}$ −70° (c 1, chloroform);

$^1$H-NMR spectrum (in deutero-chloroform, TMS as internal standard):

δ 2.00 (1H, dd, OH-5), 2.20 (1H, dd, $J_{OH-3,F}$=3 Hz, OH-3), 3.43 (3H, s, OCH₃), 4.78 (1H, dd, $J_{2,F}$=54 Hz, H-2), 5.02 (1H, d, $J_{1,F}$=11 Hz, H-1);

$^{19}$F-NMR spectrum (in deutero-chloroform, Freon 11 as internal standard):

δ −210.9 (dddd, J=3, 11, 23, 54 Hz).

Elemental Analysis:
Found: C 43.61%, H 6.68%, F 11.46%.
Calculated for $C_6H_{11}FO_4$: C 43.37%, H 6.67%, F 11.44%.

An alternative method for the preparation of methyl 2-deoxy-2-fluoro-D-ribofuranoside is described in the "Carbohydr. Res." 1, pp. 455–466 (1966) written by J. F. Codington, I. L. Doerr, and J. J. Fox.

(3) Synthesis of methyl 3,5-di-O-benzoyl-2-deoxy-2-fluoro-α- and -β-D-ribofuranosides [compound (6) and compound (7)]

Compounds (4), (5) → Step 4 →

Compound (6)

Compound (7)

The mixture of compounds (4) and (5) obtained in item (2) above (10.0 g) was dissolved in pyridine (200 ml), to which benzoyl chloride (17.5 ml) was then added, and the resulting mixture was allowed to stand at room temperature for 30 minutes. After addition of a small amount of water, the resultant reaction solution was concentrated, and the syrup obtained was extracted with chloroform. The solution in chloroform was washed with a 5% aqueous potassium hydrogen sulfate solution, a 5% aqueous sodium hydrogen carbonate solution and water, successively, and then dried over anhydrous sodium sulfate and concentrated to afford a mixture of the titled compounds (6) and (7) (22.3 g) as colorless crystals. Yield: 99%.

Recrystallization of the crystals so obtained from toluene-n-hexane gave compound (7) (β-isomer) as colorless needles.

Compound (7) (β-isomer):
mp. 88°–89° C.;
$[\alpha]_D^{21} +31°$ (c 1, chloroform);
$^1$H-NMR spectrum (in deutero-benzene, TMS as internal standard):
δ 4.83 (1H, d, $J_{1,F}$=10 Hz, H-1), 5.07 (1H, dd, $J_{2,F}$=53 Hz, H-2).
Elemental Analysis:
Found: C 64.12%, H 5.19%, F 5.17%.
Calculated for $C_{20}H_{19}FO_6$: C 64.17%, H 5.12%, F 5.08%.

In this connection, it is noticed that J. F. Codington, I. L. Doerr, and J. J. Fox show only the melting point of methyl 3,5-di-O-benzoyl-2-deoxy-2-fluoro-D-riboside in the "Carbohydr. Res.", 1, pp.455–466 (1966).

(4) Synthesis of 3,5-di-O-benzoyl-2-deoxy-2-fluoro-α- and -β-D-ribofuranosyl acetates [compound (8) and compound (9)]

Compounds (6), (7) $\xrightarrow{\text{Step 5}}$

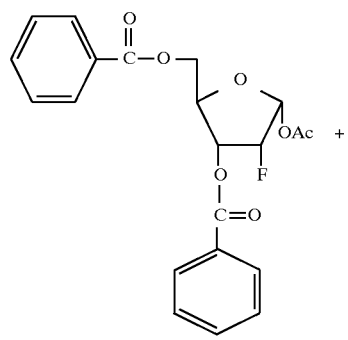

Compound (8)

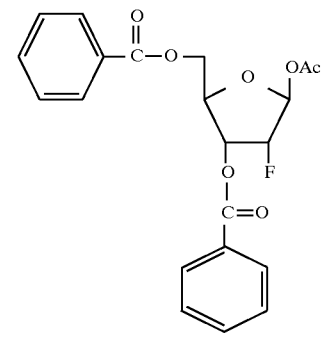

Compound (9)

The mixture of compounds (6) and (7) obtained in item (3) above (2.07 g) was dissolved in acetic acid (30 ml) and to the resulting solution, under ice-cooling, were added acetic anhydride (2 ml) and sulfuric acid (0.2 ml), and the resulting mixture was allowed to stand overnight at room temperature. The reaction solution obtained was added to a saturated aqueous solution of sodium hydrogen carbonate (400 ml) which was kept under ice-cooling condition. Insoluble material thus formed was extracted with chloroform and the solution in chloroform was washed with water, dried over anhydrous sodium suflate and then concentrated to give a pale yellow syrup.

The syrup was purified by silica gel column chromatography (developer; ethyl acetate-n-hexane, 1:3), thus affording a mixture of the titled compounds (8) and (9) (2.18 g) as a colorless solid. Yield: 98%.

$^1$H-NMR Spectrum (in deutero-chloroform, TMS as internal standard); ratio of compound (8) to compound (9)=about 1:6;
δ 1.96 [3H, s, Ac of compound (9)], 2.19 [3H, s, Ac of compound (8)], 6.38 [1H, d, $J_{1,F}$=10.5 Hz, H-1 of compound (9)], 6.53 [1H, dd, $J_{1,2}$=4, $J_{1,F}$=2 Hz, H-1 of compound (8)].

Crystallization of the solid so obtained from ether-n-hexane gave compound (9) as colorless crystals.

Compound (9) (β-isomer):
mp. 105°–106.5° C.;
$[\alpha]_D^{22} +34°$ (c 1, chloroform).
Elemental Analysis:
Found: C 62.83%, H 4.76%, F 4.52%.
Calculated for $C_{21}H_{19}FO_7$: C 62.68%, H 4.76%, F 4.72%.

(5) Synthesis of 3,5-di-O-benzoyl-2-deoxy-2-fluoro-α- and -β-D-ribofuranosyl bromides [compound (10) and compound (11)]

Compounds (8), (9) $\xrightarrow{\text{Step 6}}$

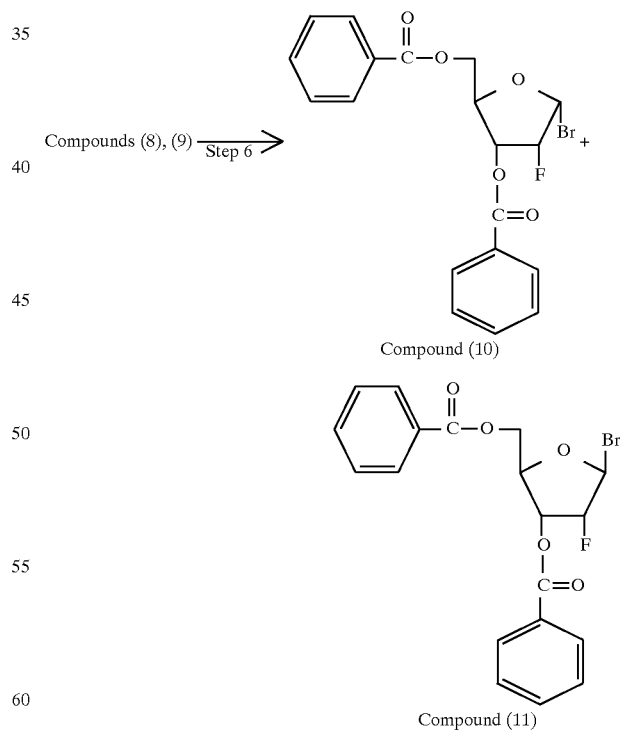

Compound (10)

Compound (11)

The mixture of compounds (8) and (9) obtained in item (4) above (3.18 g) was dissolved in dichloromethane (60 ml), to which was then added 30% hydrogen bromide-acetic acid (6 ml), and the resulting mixture was allowed to stand for reaction overnight at room temperature. The reaction solution obtained was concentrated and a small amount of the residual acetic acid was removed by azeotropic distillation with toluene, thus affording a mixture of compounds (10) and (11) (3.31 g) as a pale yellow syrup. Crude yield: 99%.

$^1$H-NMR Spectrum (in deutero-chloroform, TMS as internal standard); ratio of compound (10) to compound (11)=about 1:6;

δ 5.17 [1H, ddd, $J_{2,F}$=51 Hz, H-2 of Compound (10)], 5.62 [1H, dd, $J_{2,F}$=54 Hz, H-2 of Compound (11)], 6.52 [1H, d, $J_{1,F}$=12 Hz, H-1 of Compound (11)], 6.71 [1H, d, $J_{1,2}$=45 Hz, H-1 of compound (10)].

The syrup obtained above was crystallized from a mixture of toluene-n-hexane, affording compound (11) (β-isomer) as colorless needles.

Compound (11) (β-isomer):

mp. 92°–93.5° C.;

$[α]_D^{21}$ −25° (c 1, chloroform).

Elemental Analysis:

Found: C 53.89%, H 3.84%, Br 18.78%, F 4.65%.

Calculated for $C_{19}H_{16}BrFO_5$: C 53.92%, H 3.81%, Br 18.88%, F 4.49%.

(6) Synthesis of 3,5-di-O-benzoyl-2-deoxy-2-fluoro-α- and -β-D-ribofuranosyl azides [compound (12) and compound (13)]

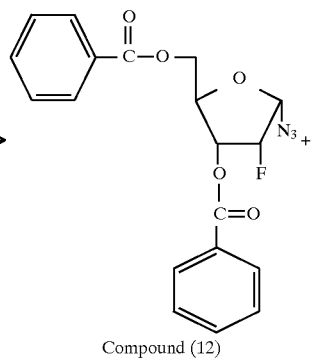

Compound (12)

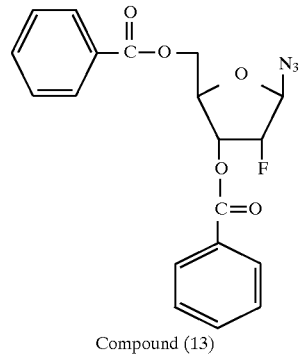

Compound (13)

The mixture of compounds (10) and (11) (2.02 g) obtained in item (5) above was dissolved in acetonitrile (40 ml), and to the resultant solution were added sodium azide (476 mg) and tetraethylammonium bromide (1.03 g). The mixture obtained was kept at room temperature under stirring for 5 hours to effect the reaction. The reaction solution as formed was concentrated to a small volume and then diluted with addition of chloroform. The solution in chloroform was washed with water, dried over anhydrous sodium sulfate and concentrated to give a mixture of the titled compounds (12) and (13) [ratio of compound (12) to compound (13)=1.2:1] (1.80 g) as a colorless syrup. Yield: 98%.

Separation of the syrup by silica gel column chromatography (developer; chloroform) gave compound (12) as a colorless syrup and compound (13) as colorless needles.

Compound (12) (α-isomer):

$[α]_D^{23}$ +150° (c 1, chloroform);

IR: 2120 cm$^{-1}$($N_3$);

$^1$H-NMR spectrum (in deutero-chloroform, TMS as internal standard):

δ 5.26 (1H, ddd, $J_{2,F}$=52 Hz, H-2), 5.46 (1H, dd, $J_{1,2}$=4, $J_{1,F}$=9 Hz, H-1);

$^{19}$F-NMR spectrum (in deutero-chloroform, Freon 11 as internal standard):

δ −212.6 (ddd).

Elemental Analysis:

Found: C 59.22%, H 4.21%, F 4.78%, N 10.68%.

Calculated for $C_{19}H_{16}FN_3O_5$: C 59.22%, H 4.19%, F 4.93%, N 10.90%.

Compound (13) (β-isomer):

mp. 64°–65° C. (measured after recrystallization from n-hexane);

$[α]_D^{23}$ −107° (c 1, chloroform);

IR: 2120 cm$^{-1}$ ($N_3$);

$^1$H-NMR spectrum (in deutero-chloroform, TMS as internal standard):

δ 5.09 (1H, dd, $J_{2,F}$=53 Hz, H-2), 5.66 (1H, d, $J_{1,F}$=13 Hz, H-1);

$^{19}$F-NMR spectrum (in deutero-chloroform, Freon 11 as internal standard):

δ −205.8 (ddd).

Elemental Analysis:

Found: C 59.20%, H 4.21%, F 4.70%, N 11.02%.

Calculated for $C_{19}H_{16}FN_3O_5$: C 59.22%, H 4.19%, F 4.93%, N 10.90%.

(7) Synthesis of ethyl 5-amino-1-(3,5-di-O-benzoyl-2-deoxy-2-fluoro-α- and -β-D-ribofuranosyl)imidazole-4-carboxylates [compounds (15) and (16)]

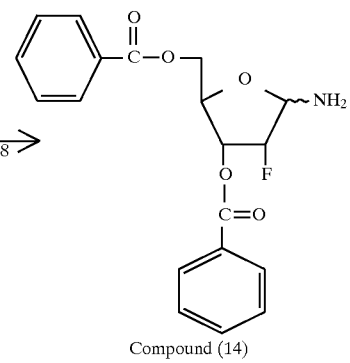

Compound (14)

Compound (14) + NC—CH—COOC$_2$H$_5$ 
              |
              N
              ‖
              CH(OC$_2$H$_5$)

-continued

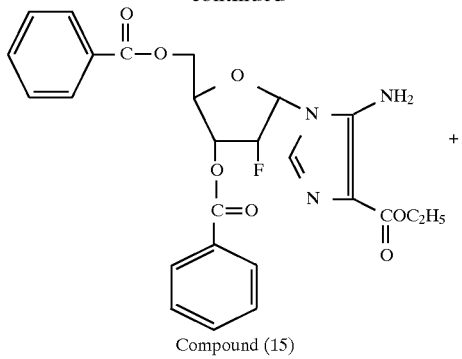

Compound (15)

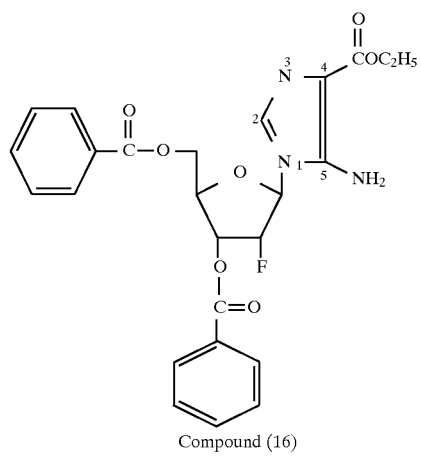

Compound (16)

The mixture of compounds (12) and (13) so obtained in item (6) above (1.16 g) was dissolved in dioxane (25 ml) and the resulting solution was subjected to catalytical reduction by blowing hydrogen therein at room temperature for 1 hour in the presence of palladium black as catalyst. The resulting reaction solution containing the glycosylamine compound (14) thus formed was filtered and the filtrate was concentrated to about ½ volume and then diluted with addition of chloroform (200 ml). The solution obtained was dried over anhydrous sodium sulfate and then concentrated to give the glycosylamine compound (14) as a colorless syrup.

This syrup was dissolved in dichloroethane (10 ml), to which was then added a solution of ethyl N-(α-cyano-α-ethoxycarbonylmethyl)formimidate (550 mg) in dichloroethane (5 ml), and the resulting mixture was heated under reflux for 1 hour.

The reaction solution so obtained was concentrated to give a syrup which was then subjected to silica gel column chromatography (developer; ethyl acetate-chloroform, 1:2) for the separation and purification of the desired product, thereby the titled compound (15) was obtained as a colorless solid (180 mg). Also, compound (16) was obtained as colorless crystals (285 mg). Yields of compounds (15) and (16) based on the mixture of compounds (12) and (13) were 12% for compound (15) and 19% for compound (16).

Compound (15) (α-isomer):
[α]hd D$^{22}$ +47° (c1, chloroform);
$^1$H-NMR spectrum (in deutero-chloroform, TMS as internal standard):
δ 1.36 (3H, t, —CH$_2$CH$_3$), 4.33 (2H, q, —CH$_2$CH$_3$), 5.30 (2H, s, —NH$_2$) 5.56 (1H, dt, J$_{2',F}$=52.5 Hz, H-2'), 6.11 (1H, dd, J$_{1',2'}$=3.5, J$_{1',F}$=16 Hz, H-1').
Elemental Analysis:
Found: C60.47%, H 4.95%, F 3.79%, N 8.46%.

Calculated for C$_{25}$H$_{24}$ FN$_3$O$_7$: C 60.36%, H 4.86%, F 3.82%, N 8.45%.

Compound (16)(β-isomer):
mp. 165.5°–166.5° C. (measured after recrystallization from toluene-n-hexane);
[α]$_D^{24}$ −45° (c 1, chloroform);
$^1$H-NMR spectrum (in deutero-chloroform, TMS as internal standard):
δ 1.37 (3H, t, —CH$_2$CH$_3$), 4.32 (2H, q, —CH$_2$CH$_3$), 5.14 (2H, s, —NH$_2$), 5.62 (1H, ddd, J$_{2',F}$=52.5 Hz, H-2'), 5.89 (1H, dd, J$_{1',2'}$=4, J$_{1',F}$=15 Hz, H-1'), 7.18 (1H, s, H-2).
Elemental Analysis:
Found: C 60.27%., H 5.12%, F 3.54%, N 8.49%.
Calculated for C$_{25}$H$_{24}$FN$_3$O$_7$: C 60.36%, H 4.86%, F 3.82%, N 8.45%.

(8) Synthesis of 5-amino-1-(3,5-di-O-acetyl-2-deoxy-2-fluoro-β-D-ribofuranosyl)imidazole-4-carboxylic acid [compound (18)]

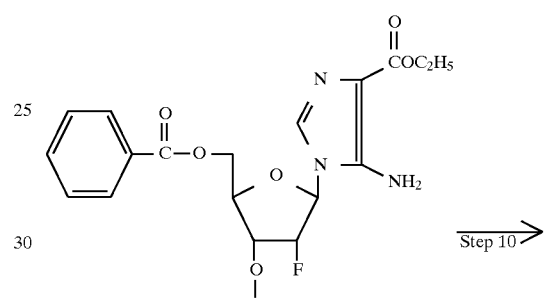

Compound (16)

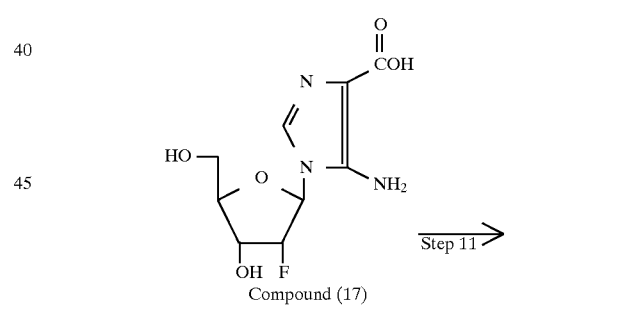

Compound (17)

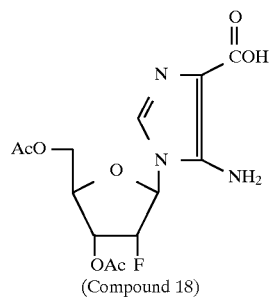

(Compound 18)

Compound (16) (312 mg) obtained in item (7) above was dissolved in a mixture of 0.6M aqueous sodium hydroxide-dioxane (1:1) (18 ml) and the resulting solution was allowed to react at 80° C. for 1 hour for removal of both the benzoyl groups and ester-forming ethyl group from compound (16).

The reaction solution obtained was neutralized with 1M hydrochloric acid, then washed with diethylether and concentrated to give a residue (460 mg) containing compound (17).

The above residue was suspended in pyridine (8 ml), to which was added acetic anhydride (4 ml) under ice-cooling, and the resulting mixture was allowed to stand at room temperature for 30 minutes for acetylation of the hydroxyl groups. The reaction solution obtained was concentrated and the resulting residue was extracted with chloroform, and the extract was filtered. The filtrate was concentrated to a small volume, to which diethylether was added to cause precipitation, and the precipitate so formed was collected, yielding the titled compound (18) (133 mg). Yield: 60%.

(9) Synthesis of 1-(3,5-di-O-acetyl-2-deoxy-2-fluoro-β-D-ribofuranosyl)-4-diazoacetyl-5-(dimethylaminomethyleneamino)imidazole [compound (20)]

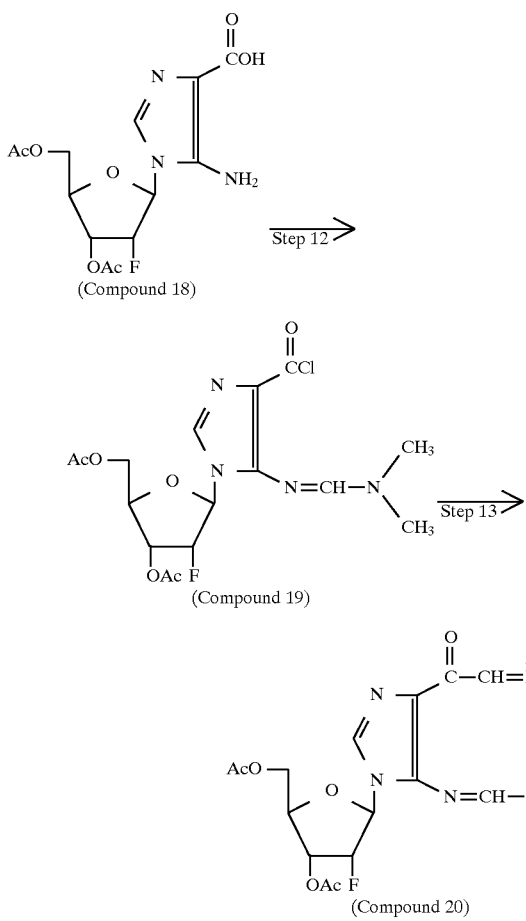

The compound (18) (62 mg) obtained in item (8) above was dissolved in tetrahydrofuran (3 ml), to which was then added N,N-dimethylchloroforminium chloride (90 mg) under ice-cooling and the resulting mixture was stirred at the same temperature as above for 30 minutes to effect both the chlorination and N,N-dimethylaminomethylenation reactions. Thus, compound (19) was produced.

The reaction solution containing compound (l) was then added to a 0.2M diazomethane solution (20 ml) in diethylether and the mixture so obtained was allowed to react at room temperature for 1 hour. The resulting reaction solution was filtered and the filtrate was concentrated to give the titled compound (20) (55 mg) as a syrup. Yield: 75%.

$^1$H-NMR Spectrum (in deutero-chloroform, TMS as internal standard)

δ 2.13, 2.15 (3Hx2, sx2, Acx2), 3.05, 3.14 [3Hx2, sx2, N(CH$_3$)$_2$], 5.44 (1H, ddd, H-2'), 6.02 (1H, dd, H-1'), 6.24 (1H, s, CHN$_2$), 7.36 (1H, s, H-2), 9.03 (1H, s, CH=N).

(10) Synthesis of 1-(3,5-di-O-acetyl-2-deoxy-2-fluoro-β-D-ribofuranosyl)-4-chloroacetyl-5-(dimethylaminomethyleneamino)imidazole [compound (21)]

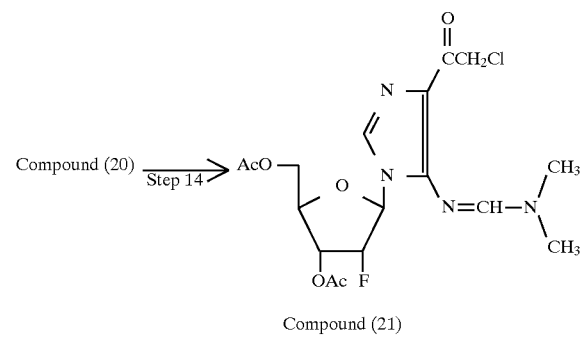

The compound (20) (21.8 mg) obtained in item (9) above was dissolved in dichloromethane (1 ml), and to the resulting solution was added a 1.25M hydrogen chloride solution (0.05 ml) in diethylether at 5° C., and the mixture so obtained was allowed to stand at that temperature overnight. The resulting reaction solution was washed with water and the organic layer obtained was dried over anhydrous sodium sulfate and concentrated to give the titled compound (21) (18.0 mg) as a syrup. Yield: 81%.

(11) Synthesis of 1-(3,5-di-O-acetyl-2-deoxy-2-fluoro-β-D-ribofuranosyl)-4-azidoacetyl-5-(dimethylaminomethyleneamino)imidazole [compound (22)]

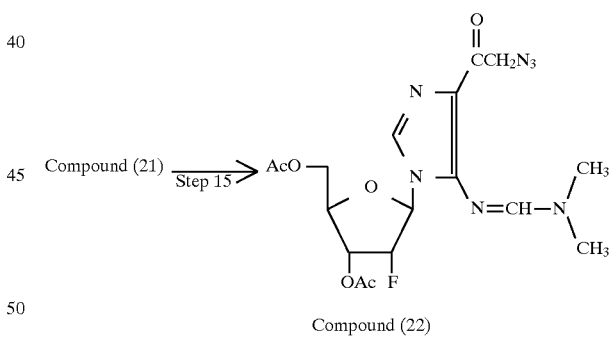

The compound (21) (177 mg) obtained in item (10) above was dissolved in N,N-dimethylformamide (3.5 ml), to which sodium azide (80 mg) was added, and the resulting mixture was stirred at room temperature for 2 hours. The reaction solution as formed was concentrated and the residue thus obtained was extracted with chloroform. The solution in chloroform was washed with water, dried over anhydrous sodium sulfate and concentrated to yield the titled compound (22) (153 mg) as a syrup. Yield: 85%.

$^1$H-NMR Spectrum (in deutero-chloroform, TMS as internal standard):

δ 2.13, 2.16 (3Hx2, sx2, Acx2), 3.07, 3.18 [3Hx2, sx2, N(CH$_3$)$_2$], 4.58 (2H, s, CH$_2$N$_3$), 5.40 (1H, dd, H-2'), 6.03 (1H, d, H-1'), 7.40 (1H, s, H-2), 9.10 (1H, s, CH=N).

(12) Synthesis of 4-azidoacetyl-1-(2-deoxy-2-fluoro-β-D-ribofuranosyl)-5-(dimethylaminomethyleneamino)imidazole [compound (23)]

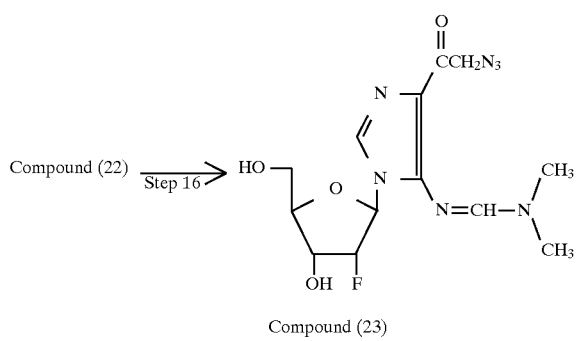

Compound (23)

The compound (22) (130 mg) obtained in item (11) above was dissolved in methanol (6 ml), to which was added a 0.2M sodium methylate solution (0.5 ml) in methanol and the resulting mixture was allowed to stand at room temperature for 30 minutes. The reaction solution as formed was neutralized with addition of ion-exchange resin, Amberlite CG-120 (H⁺form) (100–200 mesh), filtered and the filtrate was concentrated to give a solid material which was then washed with diethylether to afford the titled compound (23) (63 mg) as an insoluble substance. Yield: 60%.

(13) Synthesis of 4-aminoacetyl-1-(2-deoxy-2-fluoro-β-D-ribofuranosyl)-5-(dimethylaminomethyleneamino)imidazole [compound (24)]

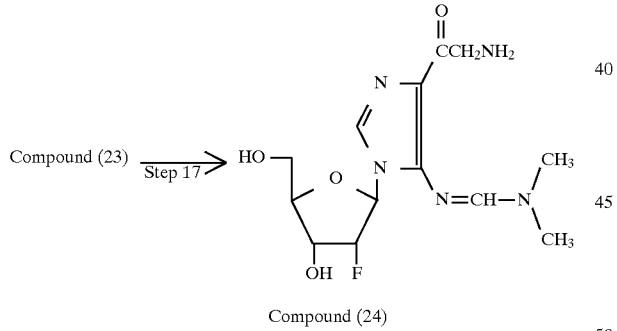

Compound (24)

The compound (23) (52 mg) obtained in item (12) above was dissolved in methanol (6 ml), and the solution was subjected to catalytic reduction by blowing hydrogen therein in the presence of palladium black as catalyst at room temperature for 30 minutes. The resulting reaction solution was filtered and the filtrate was concentrated to give a solid. The solid material thus obtained was washed with ethyl acetate to yield the titled compound (24) (43 mg) as an insoluble substance. Yield: 89%.

(14) Synthesis of 3-(2-deoxy-2-fluoro-β-D-ribofuranosyl)-6,7-dihydroimidazo[4,5-d][1,3]diazepin-8(3H)-one [compound (25)]

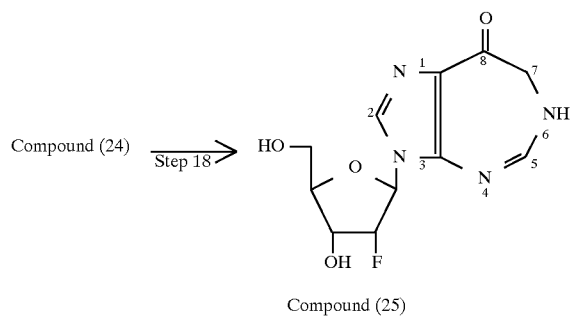

Compound (25)

The compound (24) (20 mg) obtained in item (13) above was dissolved in methanol (0.4 ml), to which was added a 0.2M sodium methylate solution (0.4 ml) in methanol and the resulting mixture was allowed to stand at room temperature overnight. The reaction solution obtained was neutralized with addition of dry ice, then concentrated to leave a residue and the residue was purified by silica gel column chromatography (developer; chloroform-methanol, 4:1), affording the titled compound (25) (6.2 mg) as a colorless solid. Yield: 36%.

¹H-NMR Spectrum (in deutero-dimethylsulfoxide, TMS as internal standard):
δ 3.78 (2H, s, $COCH_2$), 5.15 (1H, dt, H-2'), 6.15 (1H, dd, H-1'), 7.48 (1H, s, H-5), 7.94 (1H, s, H-2).

(15) Synthesis of 2'-deoxy-2'-fluorocoformycin [compound (26)] and 2'-deoxy-8-epi-2'-fluorocoformycin [compound (27)]

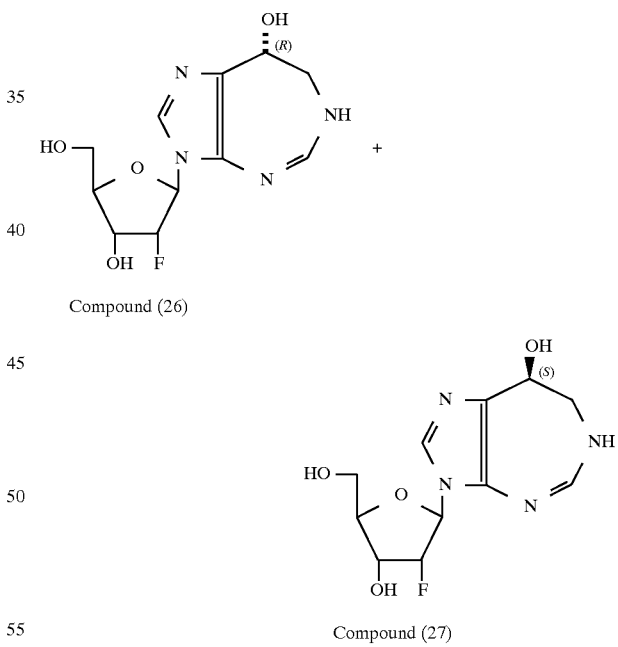

Compound (26)

Compound (27)

The compound (25) (2.2 mg) obtained in item (14) above was dissolved in a mixture of water-methanol (1:1) (0.08 ml), to which was added sodium borohydride (0.3 mg) and the resulting mixture was allowed to stand at room temperature for 15 minutes. To the reaction solution so obtained, dry ice was added to decompose the excess reagent present, and all the resulting solution was subjected to preparative high performance liquid chromatography using a reverse phase column (YMC-PACK S-343 I-15 ODS) (mobile phase; water-methanol, 4:1) to effect the separation and purification of the desired products.

Occurrence of the elution was in the order of compound (26) (k'=0.7) and compound (27) (k'=0.9), and each of the eluates was lyophilized to give separately the titled compound (26) (0.6 mg; yield 27%) as a colorless solid and the titled compound (27) (0.6 mg; yield 27%) as a colorless solid, respectively.

Compound (26) had the following physical properties:

$[\alpha]_D^{22}$ +12° (c 0.1, water);

$^1$H-NMR spectrum (in deuterium oxide, TMS as internal standard):

δ 3.38 (1H, d, H-7a), 3.50 (1H, dd, H-7b), 3.81 (1H, dd, H-5'a), 3.95 (1H, dd, H-5'b), 4.19 (1H, broad, H-4'), 4.50 (1H, ddd, H-3'), 5.14 (1H, d, H-8), 5.33 (1H, ddd, H-2'), 6.17 (1H, dd, H-1'), 7.20 (1H, s, H-5), 7.65 (1H, s, H-2);

$J_{1',2'}$=2.5, $J_{2',3'}$=4.5, $J_{3',4'}$=7.5, $J_{4',5'a}$=4, $J_{4',5'b}$=2.5, $J_{5'a,5'b}$=13, $J_{7a,7b}$=13.5, $J_{7b,8}$=4, $J_{1',F}$=18, $U_{2',F}$=53, $J_{3',F}$=19 Hz.

Compound (27) had the following physical properties:

$[\alpha]_D^{22}$ -115° (c 0.09, water);

$^1$H-NMR spectrum (in deuterium oxide, TMS as internal standard):

δ 3.38 (1H,d,H-7a), 3.50 (1H, dd, H-7b), 3.80 (1H, dd, H-5'a), 3.94 (1H, dd, H-5'b), 4.19 (1H, broad, H-4'), 4.52 (1H, ddd, H-3'), 5.14 (1H, d, H-8), 5.37 (1H, ddd, H-2'), 6.17 (1H, dd, H-1'), 7.20 (1H, s, H-5), 7.65 (1H, s, H-2).

$J_{1',2'}$=2.5, $J_{2',3'}$=4.5, $J_{3',4'}$=7, $J_{4',5'a}$=4, $J_{4',5'b}$=2.5, $J_{5'a,5'b}$=13, $J_{7a,7b}$=13.5, $:U_{7b,8}$=4, $J_{1',F}$=18, $J_{2',F}$=53, $J_{3',F}$=18.5 Hz.

EXAMPLE 2

(1) Synthesis of 3,5-di-O-benzoyl-2-deoxy-2-fluoro-α- and -β-D-arabinofuranosyl azides [compounds (29) and (30)]

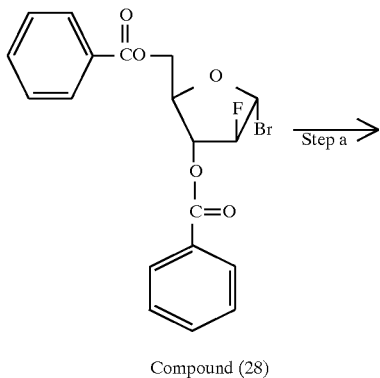

Compound (28)

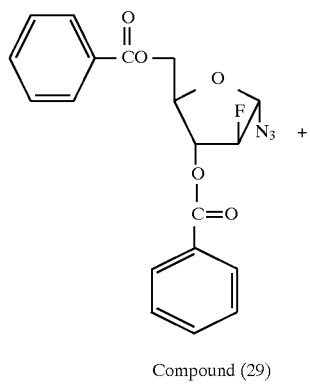

Compound (29)

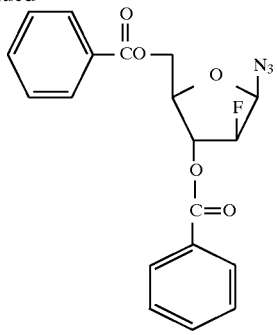

Compound (30)

3,5-Di-O-benzoyl-2-deoxy-2-fluoro-α-D-arabinofuranosyl bromide [namely, compound (28); this compound was described by C. H. Tann et al., "J. Org. Chem.", 50, pp. 3644–3647 (1985)] (11.4 g) was dissolved in acetonitrile (230 ml). To this solution were added sodium azide (2.64 g) and tetraethylammonium bromide (5.80 g), and the resulting mixture was allowed to react at room temperature under stirring for 2 hours.

The reaction solution so obtained was concentrated to a small volume, to which chloroform was added and the resulting solution in chloroform was washed with water, dried over anhydrous sodium sulfate and concentrated to afford a mixture of the titled compounds (29) and (30) [at a ratio between compounds (29) and (30)=1.4:1] as a colorless syrup (10.2 g). Yield: 98%. This syrup was subjected to silica gel column chromatography (developer; ethyl acetate-n-hexane, 1:4) for separation of the desired compounds, affording compound (29) as a colorless syrup and compound (30) as colorless crystals.

Compound (29) (α-isomer):

$[\alpha]_D^{23}$ +150° (c 1, chloroform);

IR: 2110 cm$^{-1}$ ($N_3$);

$^1$H-NMR spectrum (in deutero-chloroform, TMS as internal standard):

δ 5.05 (1H, d, $J_{2,F}$=49.5 Hz, H-2), 5.76 (1H, d, $J_{1,F}$=12.5 Hz, H-1);

$^{19}$F-NMR spectrum (in deutero-chloroform, Freon 11 as internal standard):

δ -187.6 (ddd).

Elemental Analysis:
Found: C 59.56%, H 4.45%, F 5.32%, N 11.22%.
Calculated for $C_{19}H_{16}FN_3O_5$: C 59.22%, H 4.19%, F 4.93% N. 10.90%.

Compound (30) (β-isomer):

mp. 88°–89° C. (measured after recrystallization from n-hexane);

$[\alpha]_D^{23}$ -106° (c 1, chloroform);

IR: 2120 cm$^{-1}$ ($N_3$);

$^1$H-NMR spectrum (in deutero-chloroform, TMS as internal standard, $^{19}$F-broad band decoupling method):

δ 5.23 (1H, t, $J_{1,2}$=$J_{2,3}$=4 Hz, H-2), 5.32 (1H, d, H-1);

$^{19}$F-NMR spectrum (in deutero-chloroform, Freon 11 as internal standard):

δ -202.5.

Elemental Analysis:
Found: C 59.32%, H 4.20%, F 4.72%, N 11.04%.
Calculated for $C_{19}H_{16}FN_3O_5$: C 59.22%, H 4.19%, F 4.93% N 10.90%.

(2) Synthesis of ethyl 5-amino-1-(3,5-di-O-benzoyl-2-deoxy-2-fluoro-α- and -β-D-arabinofuranosyl)imidazole-4-carboxylates [compounds (32) and (33)]

Compounds (29), (30) →Step b→

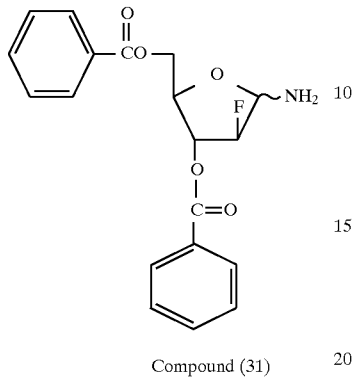

Compound (31)

Compound (31) + NC—CH—COOC₂H₅
                    |
                    N=CH(OC₂H₅)   →Step c→

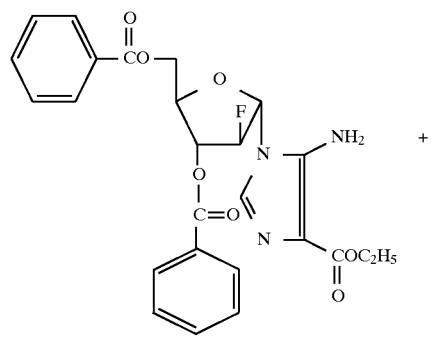

Compound (32)

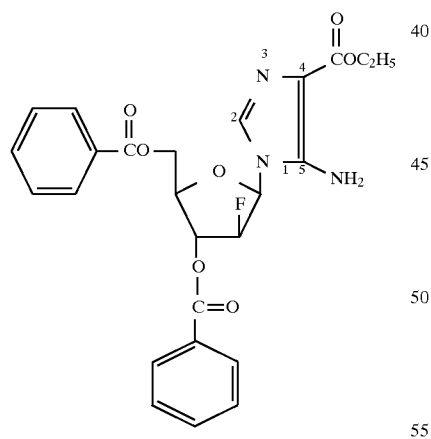

Compound (33)

The mixture of compounds (29) and (30) (1.00 g) obtained in item (1) as above was dissolved in dioxane (20 ml), and the resulting solution was subjected to catalytic reduction by blowing hydrogen therein in the presence of palladium black as catalyst at room temperature for 1 hour. The reaction solution as formed was filtered and the filtrate was concentrated to about ½ volume and then diluted with addition of chloroform (200 ml). The diluted solution was dried over anhydrous sodium sulfate and then concentrated to yield glycosylamine compound (31) as a colorless syrup.

This syrup was dissolved in dichloroethane (10 ml), to which was then added a solution of ethyl N-(α-cyano-α-ethoxycarbonylmethyl)formimidate (500 mg) in dichloroethane (5 ml), and the resulting mixture was heated under reflux for 1 hour.

The reaction solution so obtained was concentrated and the resulting syrup was subjected to silica gel column chromatography (developer; ethyl acetate-chloroform, 1:2) for separation and purification of the desired products, whereby affording the titled compound (32) (298 mg) as colorless crystals and the titled compound (33) (302 mg) as a colorless solid.

Yields based on the mixture of compounds (29) and (30) were 23% for compound (32) and 23% for compound (33)

Compound (32) (α-isomer):

mp. 176°–177° C. (measured after recrystallization from chloroform-n-hexane);

$[\alpha]_D^{23}$ +41° (c 1, chloroform);

¹H-NMR spectrum (in deutero-chloroform, TMS as internal standard):
  δ 1.38 (3H, t, —CH₂CH₃), 4.34 (2H, q, —CH₂CH₃), 5.28 (2H, s, NH₂), 5.77 (1H, dt, H-2'), 6.07 (1H, dd, H-1'), 7.27 (1H, s, H-2);

$J_{1',2'}=2$, $J_{1',F}=16$, $J_{2',F}=49.5$ Hz;

¹⁹F-NMR spectrum (in deutero-chloroform, Freon 11 as internal standard):
  δ –187.7 (ddd).

Elemental Analysis:
  Found: C 60.32%, H 5.09%, F 4.05%, N 8.65%.
  Calculated for C₂₅H₂₄FN₃O₇: C 60.36%, H 4.86%, F 3.82%, N 8.45%.

Compound (33) (β-isomer):

$[\alpha]_D^{23}$ –26° (c 1, chloroform);

¹H-NMR spectrum (in deutero-chloroform, TMS as internal standard):
  δ 1.36 (3H, t, —CH₂CH₃), 4.32 (2H, q, —CH₂CH₃), 5.33 (2H, s, NH₂), 5.38 (1H, ddd, $J_{2',F}$=50 Hz, H-2'), 5.91 (1H, dd, $J_{1',2'}$=2.5, $J_{1',F}$=22.5 Hz, H-1'), 7.24 (1H, d, $J_{2,F}$=2 Hz, H-2);

¹⁹F-NMR spectrum (in deutero-chloroform, Freon 11 as internal standard):
  δ –198.5 (dddd).

Elemental Analysis:
  Found: C 59.10%, H 5.35%, F 3.70%, N 8.64%.
  Calculated for C₂₅H₂₄FN₃O₇·0.5H₂O: C 59.29%, H 4.98%, F 3.75%, N 8.30%.

(3) Synthesis of 5-amino-1-(3,5-di-O-acetyl-2-deoxy-2-fluoro-β-D-arabinofuranosyl)imidazole-4-carboxylic acid [compound (35)]

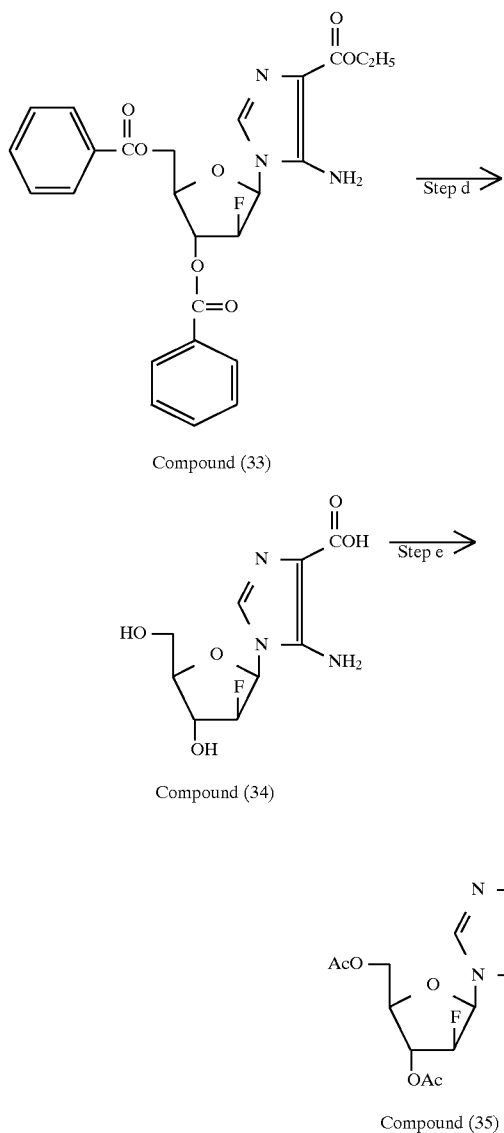

Compound (33)

Compound (34)

Compound (35)

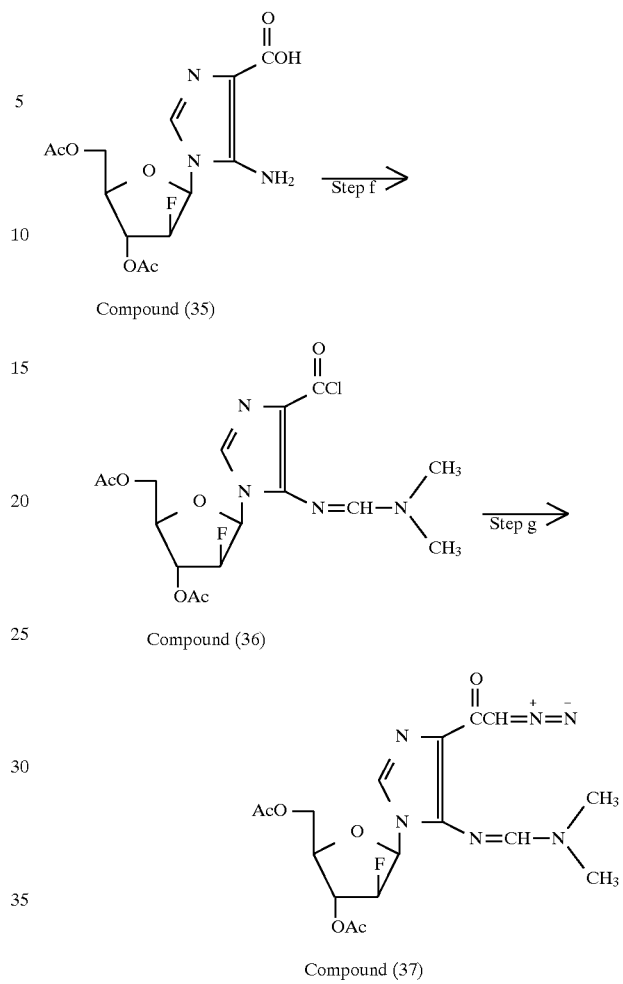

Compound (35)

Compound (36)

Compound (37)

Compound (33) (255 mg) obtained in item (2) above was dissolved in a mixture of 0.6M aqueous sodium hydroxide and dioxane (1:1) (15 ml), and the resulting solution was allowed to react at 80° C. for 1 hour. The reaction solution containing compound (34) thus produced was neutralized by addition of 1M hydrochloric acid. The aqueous solution so obtained was washed with diethylether and then concentrated to leave a residue (380 mg) which contained compound (34).

The residue was suspended in pyridine (7 ml), to which acetic anhydride (3.5 ml) was added under ice-cooling and the resulting mixture was allowed to react at room temperature for 30 minutes. The resulting reaction solution was concentrated and the residue so obtained was extracted with chloroform. The solution in chloroform was filtered and the filtrate was concentrated to a small volume, to which was then added diethylether to cause precipitation and the precipitate formed was collected to afford the titled compound (35) (105 mg). Yield: 58%.

(4) Synthesis of 1-(3,5-di-O-acetyl-2-deoxy-2-fluoro-β-D-arabinofuranosyl)-4-diazoacetyl-5-(dimethylaminomethyleneamino)imidazole [compound (37)]

Compound (35) (93 mg) obtained in item (3) above was dissolved in tetrahydrofuran (4.5 ml), to which was then added N,N-dimethylchloroforminium chloride (135 mg) under ice-cooling. The resulting mixture was allowed to undergo the reaction for 30 minutes. The reaction solution containing compound (36) thus produced was then added to a 0.2M diazomethane solution (30 ml) in diethylether and the reaction was maintained at room temperature for 1 hour. The reaction solution so obtained was filtered and the filtrate was concentrated to give the titled compound (37) (83 mg) as a syrup. Yield: 75%.

$^1$H-NMR Spectrum (in deutero-chloroform, TMS as internal standard):

δ 2.11, 2.16 (3Hx2, sx2, Acx2), 3.05, 3.15 [3Hx2, sx2, N(CH$_3$)$_2$], 5.02 (1H, ddd, H-2'), 6.19 (1H, dd, H-1'), 6.27 (1H, s, CHN$_2$), 7.41 (1H, d, H-2), 9.04 (1H, s, CH=N).

(5) Synthesis of 1-(3,5-di-O-acetyl-2-deoxy-2-fluoro-β-D-arabinofuranosyl)-4-chloroacetyl-5-(dimethylaminomethyleneamino)imidazole [compound (38)]

Compound (37) →$_{\text{step h}}$

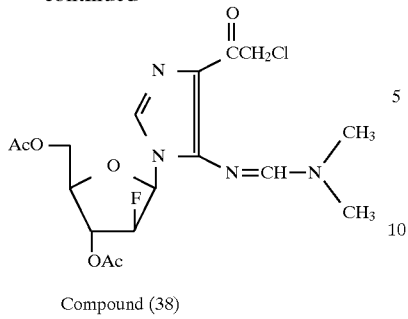

Compound (38)

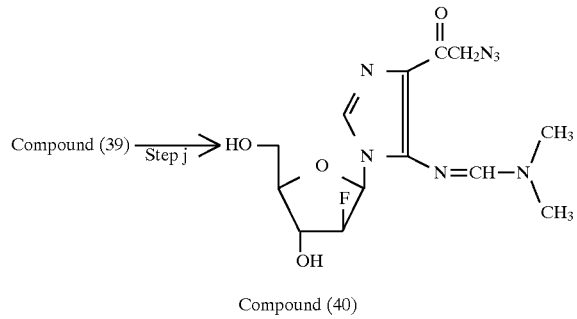

Compound (40)

Compound (37) (80 mg) obtained in item (4) above was dissolved in dichloromethane (4 ml), to which was added at 5° C. a 1.25M hydrogen chloride solution (0.2 ml) in diethylether and the mixture obtained was allowed to undergo the reaction at that temperature overnight. The resulting reaction solution was washed with water, and the organic layer was dried over anhydrous sodium sulfate and then concentrated to give the titled compound (38) (61 mg) as a syrup. Yield: 75%.

(6) Synthesis of 1-(3,5-di-O-acetyl-2-deoxy-2-fluoro-β-D-arabinofuranosyl)-4-azidoacetyl-5-(dimethylaminomethyleneamino)imidazole [compound (39)]

Compound (38) $\xrightarrow{\text{Step i}}$

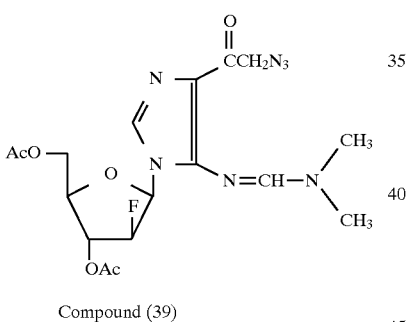

Compound (39)

Compound (38) (60 mg) obtained in item (5) above was dissolved in N,N-dimethylformamide (1.2 ml), to which sodium azide (27 mg) was added and the mixture so obtained was stirred at room temperature for 2 hours. The resulting reaction solution was concentrated and the residue as formed was extracted with chloroform. The solution in chloroform thus formed was washed with water, dried over anhydrous sodium sulfate and then concentrated to afford the titled compound (39) (56 mg) as a syrup. Yield: 92%.

$^1$H-NMR Spectrum (in deutero-chloroform, TMS as internal standard):
δ 2.11, 2.16 (3Hx2, sx2, Acx2), 3.05, 3.18 [3Hx2, sx2, N(CH$_3$)$_2$], 4.62(2H, s, CH$_2$N$_3$), 5.04 (1H, dd, H-2'), 6.19 (1H, dd, H-1'), 7.44 (1H, d, H-2), 9.09 (1H, S, CH=N).

(7) Synthesis of 4-azidoacetyl-1-(2-deoxy-2-fluoro-β-D-arabinofuranosyl)-5-(dimethylaminomethyleneamino)imidazole [compound (40)]

Compound (39) (50 mg) obtained in item (6) above was dissolved in methanol (2 ml), to which was then added a 0.2M sodium methylate solution (0.2 ml) in methanol. The mixture obtained was allowed to undergo the reaction at room temperature for 20 minutes. The resulting reaction solution was neutralized with addition of ion-exchange resin, Amberlite CG-120 (H$^+$ form) (100–200 mesh) and filtered, and the filtrate was concentrated. The solid residue obtained was washed with diethylether to give the titled compound (40) (31 mg) as an insoluble solid. Yield: 77%.

(8) Synthesis of 4-aminoacetyl-1-(2-deoxy-2-fluoro-β-D-arabinofuranosyl)-5-(dimethylaminomethyleneamino)imidazole [compound (41)]

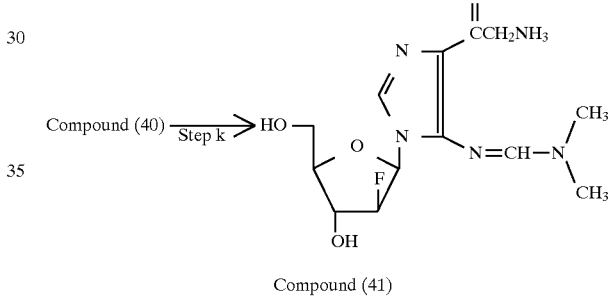

Compound (41)

The compound (40) (35 mg) obtained in item (7) above was dissolved in methanol (3.5 ml) and the resulting solution was subjected to catalytical reduction by blowing hydrogen therein in the presence of palladium black as catalyst at room temperature for 30 minutes. The reaction solution was filtered and the filtrate was concentrated. The resulting solid was washed with ethyl acetate to yield the titled compound (41) (29.7 mg) as an insoluble solid. Yield: 92%.

(9) Synthesis of 3-(2-deoxy-2-fluoro-β-D-arabinofuranosyl)-6,7-dihydroimidazo[4,5-d][1,3]diazepin-8(3H)-one [compound (42)]

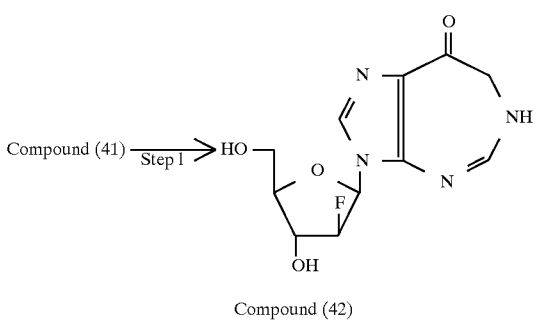

Compound (42)

Compound (41) (18 mg) obtained in item (8) above was dissolved in a 0.1M sodium methylate solution (0.72 ml) in methanol, and the resultant solution was allowed to stand at room temperature overnight. The reaction solution as formed was neutralized with addition of dry ice and then concentrated to leave a residue. The residue was purified by silica gel column chromatography (developer: the lower layer of water-methanol-chloroform, 1:2:4), affording the titled compound (42) (4.7 mg) as a colorless solid. Yield: 30%.

$^1$H-NMR Spectrum (in deutero-dimethylsulfoxide, TMS as internal standard):

δ 3.79 (2H, d, COCH$_2$), 5.05 (1H, dt, H-2'), 6.32 (1H, dd, H-1'), 7.46 (1H, d, H-5), 7.73 (1H, d, H-2).

(10) Synthesis of 2'-deoxy-2'-epi-2'-fluorocoformycin [compound (43)] and 2'-deoxy-8,2'-diepi-2'-fluorocoformycin [compound (44)]

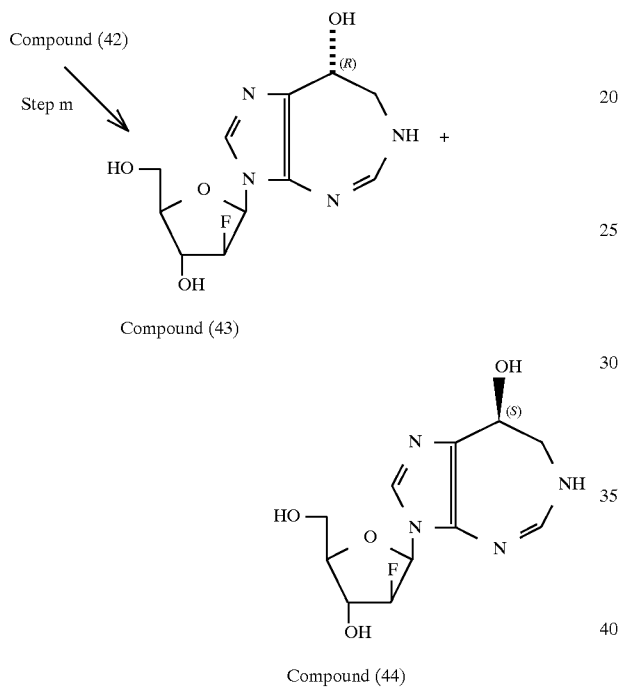

Compound (42) (3.3 mg) obtained in item (9) above was dissolved in a mixture (0.06 ml) of water-methanol (1:1). To this solution, sodium borohydride (0.4 mg) was added and the resulting mixture was allowed to undergo the reaction at room temperature for 15 minutes. Dry ice was added to the reaction solution so obtained to decompose the excess reagent present, after which the whole solution was subjected to preparative high performance liquid chromatography using a reverse phase column (YMC-PACK D-ODS-5) (mobile phase; water-methanol, 4:1) for separation and purification of the desired products.

Compound (44) (k'=0.6) and compound (43) (k'=0.8) were eluted in order, and each of the eluates was lyophilized to afford the titled compound (43) as a colorless solid (1.0 mg; yield, 30%) and compound (44) as a colorless solid (1.3 mg; yield, 39%), respectively.

Compound (43) had the following physical properties:

$[\alpha]_D^{27}$ +11820 (c 0.05, water);

$^1$H-NMR spectrum (in deuterium oxide, TMS as internal standard):

δ 3.36 (1H, d, H-7a), 3.49 (1H, dd, H-7b), 3.78 (1H, dd, H-5a), 3.86 (1H, dd, H-5b), 4.02 (1H, m, H-4'), 4.47 (1H, ddd, H-3'), 5.13 (1H, d, H-8), 5.16 (1H, ddd, H-2'), 6.27 (1H, dd, H-1'), 7.19 (1H, s, H-5), 7.70 (1H, d, H-2);

$J_{7a,7b}$=13.5, $J_{7b,8}$=4.5, $J_{2',F}$=2.5, $J_{1',2'}$=4, $J_{2',3'}$=3, $J_{3',4'}$=5, $J_{4',5'a}$=4, $J_{4',5'b}$=6, $J_{5'a,5'b}$+12.5, $J_{1',F}$=18, $J_{2',F}$=51.5, $J_{3',F}$=18.5 Hz.

Compound (44) had the following physical properties:

$[\alpha]_D^{27}$ −27° (c 0.1, water);

$^1$H-NMR spectrum (in deuterium oxide, TMS as internal standard):

δ 3.38 (1H, d, H-7a), 3.50 (1H, dd, H-7b), 3.80 (1H, dd, H-5'a), 3.88 (1H, dd, H-5'b), 4.03 (1H, m, H-4'), 4.50 (1H, ddd, H-3'), 5.14 (1H, d, H-8), 5.19 (1H, ddd, H-2'), 6.28 (1H, dd, H-1'), 7.20 (1H, s, H-5), 7.70 (1H, d, H-2);

$J_{7a,7b}$=13.5, $J_{7b,8}$=4.5, $J_{1',2'}$=4, $J_{2',3'}$=3, $J_{3',4'}$=5, $J_{4',5'a}$=4, $J_{4',5'b}$=6, $J_{5'a,5'b}$=12.5, $J_{1',F}$=18, $J_{2',F}$=51.5, $J_{3',F}$=18.5 Hz.

EXAMPLE 3

Synthesis of 2-deoxy-2-fluoro-D-arabinofuranosyl azide [compound (45)] and 2-deoxy-2-fluoro-D-arabinofuranosyl amine [compound (46)]

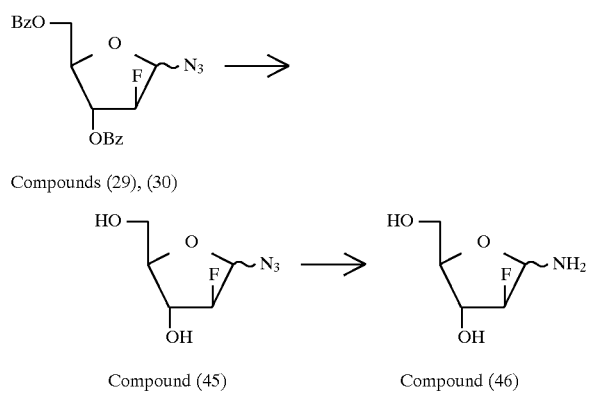

(1) A mixture (580 mg) of compounds (29) and (30) was dissolved in methanol (12 ml), and to the resulting solution was added a 0.2M sodium methylate solution (2.5 ml) in methanol, and the resulting mixture was allowed to react at room temperature for 30 minutes for methanolysis. The reaction solution was neutralized with addition of ion-exchange resin, Amberlite CG-120(H$^+$ form) (100–200 mesh), and then filtered. The filtrate was concentrated to give a syrup, followed by purifying the syrup through silica gel column chromatography (developer; toluene-ethyl acetate, 1:2) to afford the titled compound (45) (235 mg) as a colorless syrup. Yield: 88%.

$^1$H-NMR Spectrum (in deutero-dimethylsulfoxide, TMS as internal standard) (the α-isomer and β-isomer at ratio of about 1.4:1):

δ 4.74 [slightly br d, $J_{2,F}$=51.5 Hz, H-2(α)], 4.96 [dt, $J_{1,2}$=$J_{2,3}$=4, $J_{2,F}$=52 Hz, H-2(β)], 5.35 [dd, $J_{1,F}$=10 HZ, H-1(β)], 5.73 [slightly br d, $J_{1,F}$=14 Hz, H-1(α)];

$^{19}$F-NMR spectrum (in deutero-dimethylsulfoxide, Freon 11 as internal standard);

δ −185.1 [ddd, F-2(α)], −200.5 [ddd, F-2(β)].

(2) Compound (45) (65.0 mg) was dissolved in dioxane (2 ml) and the solution was catalytically reduced by blowing hydrogen therein in the presence of palladium black as catalyst at room temperature for 1 hour. The resulting reaction solution was filtered and the filtrate was concentrated to afford the titled compound (46) (51.0 mg) as a colorless solid. Yield: 92%.

Industrial Utilizability

2'-Deoxy-2'-fluorocoformycin and 2'-deoxy-8-epi-2'-fluorocoformycin, as well as 2'-deoxy-2'-epi-2'-fluorocoformycin and 2'-deoxy-8,2'-diepi-2'-fluorocoformycin which are now synthesized according to this invention are novel compounds and possess high enzyme-inhibitory activities against adenosine deaminase. In particular, these novel compounds are useful compounds which have therapeutic effects on acute lymphocytic leukemias owing to their high activities inhibitory to adenosine deaminase. Further, a variety of useful intermediates, as novel compounds, have been obtained in the course of the synthesis of the above-mentioned novel 2'-fluoro derivatives of coformycin.

We claim:
1. 2'-Deoxy-2'epi-2'-fluorocoformycin of formula (Ib')

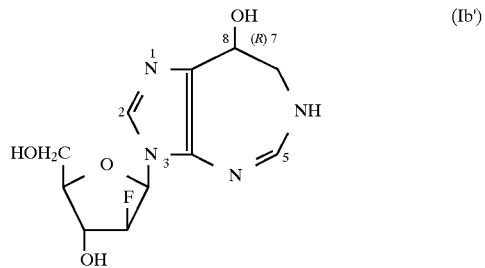

wherein the hydroxyl group at the 8-position has (R)-configuration.

* * * * *